United States Patent
Tomiyama et al.

(10) Patent No.: US 6,903,111 B2
(45) Date of Patent: Jun. 7, 2005

(54) ISOQUINUCLIDINE DERIVATIVE PROCESS FOR PRODUCING THE SAME, AND MEDICINAL COMPOSITION CONTAINING THE SAME

(75) Inventors: Hiroshi Tomiyama, Nagano (JP); Yoshinori Kobayashi, Nagano (JP); Atsushi Noda, Nagano (JP)

(73) Assignee: Kotobuki Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/467,719

(22) PCT Filed: Mar. 25, 2002

(86) PCT No.: PCT/JP02/02847

§ 371 (c)(1),
(2), (4) Date: Aug. 12, 2003

(87) PCT Pub. No.: WO02/076981

PCT Pub. Date: Oct. 3, 2002

(65) Prior Publication Data

US 2004/0067911 A1 Apr. 8, 2004

(30) Foreign Application Priority Data

Mar. 26, 2001 (JP) ........................................ 2001-088653

(51) Int. Cl.[7] .................... A61K 31/439; C07D 453/06; A61P 3/10
(52) U.S. Cl. .................... 514/299; 546/112; 546/23
(58) Field of Search ............................ 546/112; 514/299

(56) References Cited

U.S. PATENT DOCUMENTS

| | | |
|---|---|---|
| 3,535,313 A | 10/1970 | Dietrich |
| 4,028,364 A | 6/1977 | Adelstein |
| 4,134,890 A | 1/1979 | Yonan |
| 4,959,372 A | 9/1990 | Vincent et al. |
| 5,019,580 A | 5/1991 | Iwu |
| 5,021,425 A | 6/1991 | Teisseire |

FOREIGN PATENT DOCUMENTS

WO    WO 01/15673    3/2001

*Primary Examiner*—Evelyn Mei Huang
(74) *Attorney, Agent, or Firm*—Sherman & Shalloway

(57) ABSTRACT

An isoquinuclidine derivative represented by the following general formula (I): (I) [wherein $A_1$ is methylene or carbonyl]: $R_1$ is hydrogen or methyl: $R_2$ is —$(CH_2)_n$-$A_2$-Ph (n is an integer of 0 to 3 and $A_2$ is a single bond or —O—): and $R_3$ is —COOH, —COOR$_4$, —COSR$_4$ ($R_4$ is lower alkyl, unsubstituted phenyl, or phenyl substituted by a lower alkyl, lower alkoxy, hydroxyl, methoxycarbonyl, ethoxycarbonyl, or trifluoromethanesulfonamide group or by a halogen atom), etc.] or a pharmaceutically acceptable salt of the compound. Also provided is an oral remedy for diabetes, which contains the compound and has hypoglycemic activity.

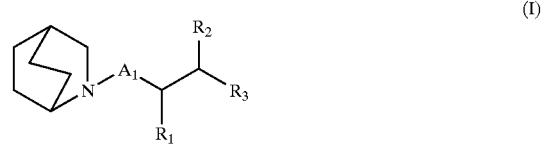

(I)

12 Claims, No Drawings

ISOQUINUCLIDINE DERIVATIVE PROCESS FOR PRODUCING THE SAME, AND MEDICINAL COMPOSITION CONTAINING THE SAME

CROSS REFERENCE TO RELATED APPLICATION

This application is a § 371 application of PCT/JP02/02847 filed on Mar. 25, 2002, which claims foreign priority to JP 2001/88635 filed on Mar. 26, 2001.

FIELD OF THE INVENTION

This invention relates to the novel isoquinuclidine derivatives which have an blood glucose lowering effect, or the pharmaceutically acceptable salts using as therapeutic and preventive agents of diabetes or diabetic complications, and the production method, further relates to a pharmaceutical composition containing these isoquinuclidine derivatives or the salts as active ingredients.

BACKGROUND OF THE INVENTION

In a treatment of diabetes, an improvement of life-style such as diet and exercise is important but insulin or oral antidiabetic agents have been used to gain more sufficient effect. Biguanide and sulfonylurea derivatives have been used as antidiabetic agents so far, and recently, suger absorption inhibitory agents, insulin enhancing agents, and insulin-secretion stimulants have been developed.

However, sulfonylurea agents cause severe and prolonged hypoglycemia as side effect and biguanide agents also cause fatal lactic acid acidosis. Furthermore, suger absorption inhibitory agents are weakly blood glucose lowering effect and it is reported that insulin enhancing agents cause severe hepatitis. As in the present, oral antidiabetic agents which are used at present, have several defects such as the side effects. In this circumstance more safety and effective agents are desired.

The object of the present invention is the provision of the novel isoquinuclidine derivatives which have an blood glucose lowering activities, or the pharmaceutically acceptable salts using as therapeutic and preventive agents of diabetes or diabetic complications, and the production method, further a pharmaceutical composition containing these isoquinuclidine derivatives or the salts as active ingredients.

DETAILED DESCRIPTION OF THE INVENTION

After elaborated to make an oral antidiabetic drug which has a potent blood glucose lowering activity and a safety, the inventor found that the compound as show general formula (I) had shown a hypoglycemic activity.

Namely, the invention is the compounds as shown in general formula (I) and its pharmaceutically acceptable salts and a composition containing these compounds as active ingredients for a treatment and/or privention of diabetes.

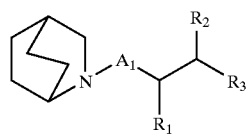

(I)

wherein, $A_1$ represents methylene or carbonyl, $R_1$ represents hydrogene or methyl group, and $R_2$ represents —$(CH_2)_n$-$A_2$-Ph (n denotes an integer of 0–3 and $A_2$ is single bond or —O—). $R_3$ represents —COOH, —COOR$_4$, or —COSR$_4$ (R$_4$ represents lower alkyl, non-substituted phenyl group, or phenyl group which is substituted with lower alkyl, lower alkoxy, hydroxy, methoxycarbonyl, ethoxycarbonyl, trifluoromethanesulfoneamide, or halogen), —CONHR$_5$ (R$_5$ represents pyridyl, thiazolyl, nonsubstituted phenyl group, or phenyl group which is substituted with lower alkyl, lower alkoxy, hydroxy, methoxycarbonyl, ethoxycarbonyl, trifluoromethanesulfoneamide, or halogen), —NHR$_6$ (R$_6$ is —SO$_2$—R$_7$ (R$_7$ represents lower alkyl, —CH$_2$COOH, trifluoromethyl, non-substituted phenyl, phenyl group which is substituted with lower alkyl, lower alkoxy, hydroxy, or halogen), or —CO—(CH$_2$)$_m$-R$_8$ (m=0 or 1, R$_8$ represents carboxyl group, non-substituted phenyl, or phenyl group which is substituted with lower alkyl, lower alkoxy, carboxyl, hydroxy, halogen, —NHSO$_2$CF$_3$, or —NHCOCOOH), —P(O)(O-iPr)$_2$, —CH(R$_9$)COOH(R$_9$ represents hydrogen, hydroxy, or —OR$_{10}$ (R$_{10}$ is lower alkyl, —CH$_2$OCH$_3$, —CH$_2$O(CH$_2$)$_2$OCH$_3$, or —CH$_2$SCH$_3$)), —CH$_2$CH(COOH)$_2$, —SO$_3$H, or a following formula

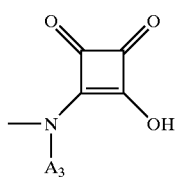

(wherein $A_3$ is hydrogen or methyl)

or a pharmaceutical acceptable salt. Oral anti-diabetic agents containing the compounds of general formula (I) or its pharmaceutically acceptable salts as active ingredients which have blood glucose lowering activity.

Typical preparation of the compounds according to the invention are shown in table 1–11, but they are not limited to these compounds.

TABLE 1

| No. | Structure | mp (° C.) |
|---|---|---|
| 1 | 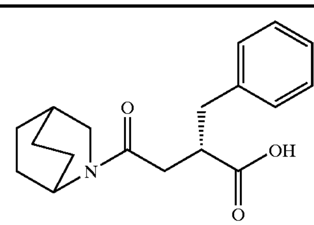 | 93–95 |
| 2 | 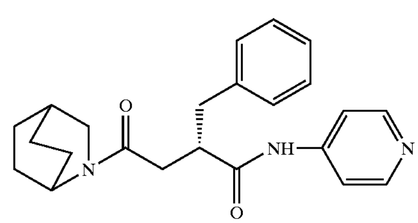 | 171–172 |

TABLE 1-continued
| No. | Structure | mp (° C.) |
|---|---|---|
| 3 | 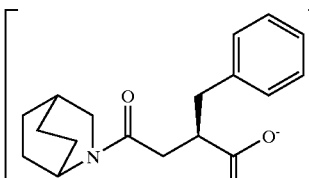 | 69–72 |
| 4 | 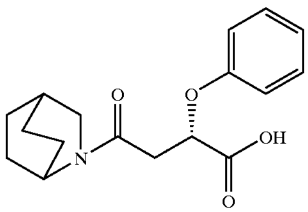 | 140–142 |
| 5 | 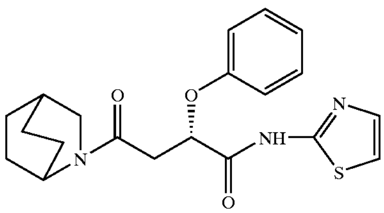 | 60–65 |
TABLE 2
| No. | Structure | mp (° C.) |
|---|---|---|
| 6 | 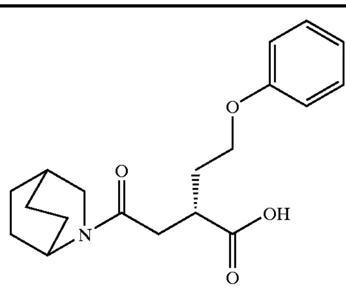 | 117–119 |
| 7 | 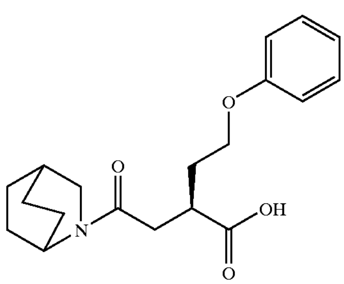 | 115–117 |
| 8 | 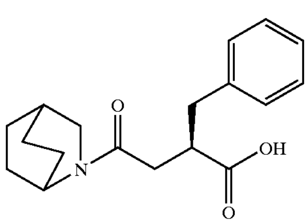 | oil |
TABLE 2-continued
| No. | Structure | mp (° C.) |
|---|---|---|
| 9 | 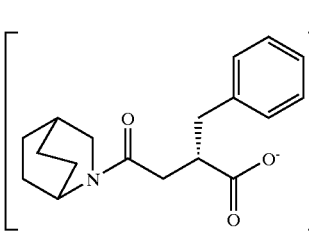 | 250–255 |
| 10 | 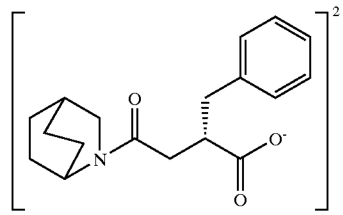 | 232–235 |
TABLE 3
| No. | Structure | mp (° C.) |
|---|---|---|
| 11 | 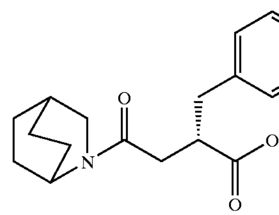 | >250 |
| 12 | 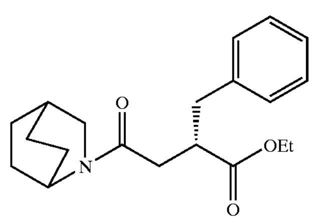 | oil |
| 13 | 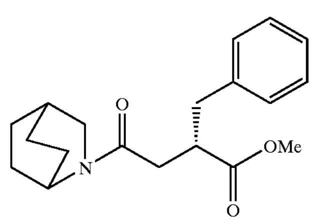 | oil |
| 14 | 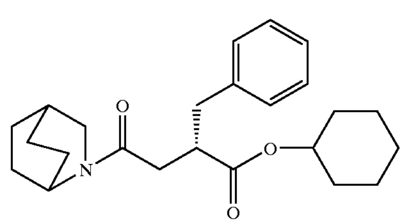 | 92–95 |

TABLE 3-continued

| No. | Structure | mp (° C.) |
|---|---|---|
| 15 | 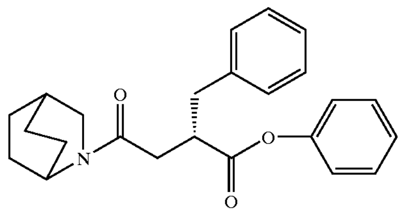 | 112–113 |

TABLE 4

| No. | Structure | mp (° C.) |
|---|---|---|
| 16 | 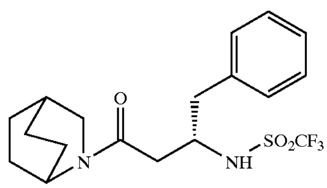 | 155–158 |
| 17 | 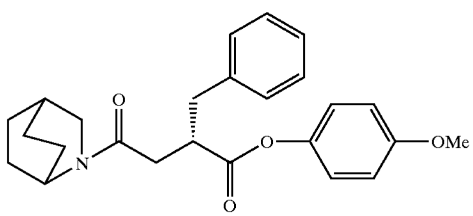 | oil |
| 18 | 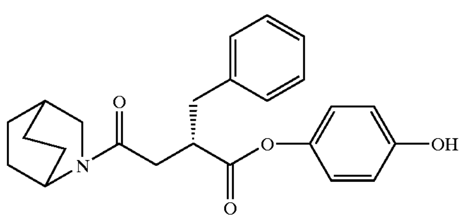 | 61–64 |
| 19 | 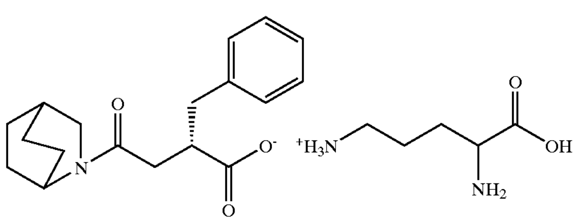 | 130–132 |
| 20 | 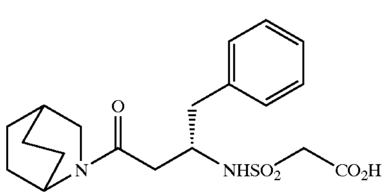 | 190–192 |

TABLE 5
| No. | Structure | mp (° C.) |
|---|---|---|
| 21 | 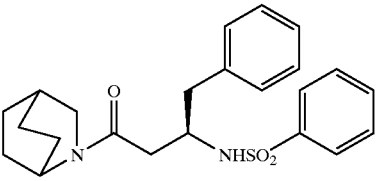 | 156–159 |
| 22 | | 149–151 |
TABLE 5-continued
| No. | Structure | mp (° C.) |
|---|---|---|
| 23 | 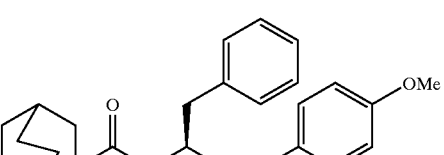 | 127–129 |
| 24 | 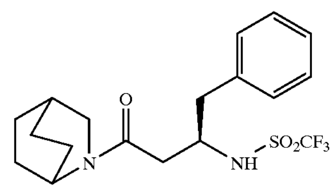 | 128–130 |
| 25 | 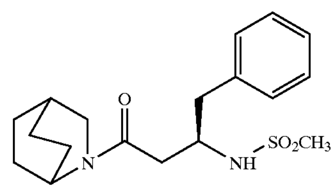 | 129–130 |
TABLE 6
| No. | Structure | mp (° C.) |
|---|---|---|
| 26 | 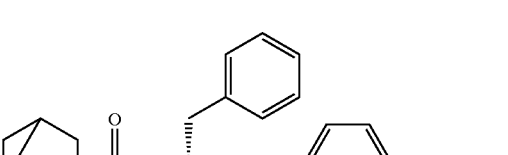 | 129–130 |
| 27 | 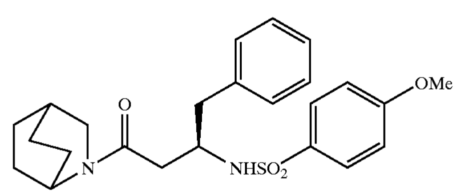 | 128–129 |
| 28 | 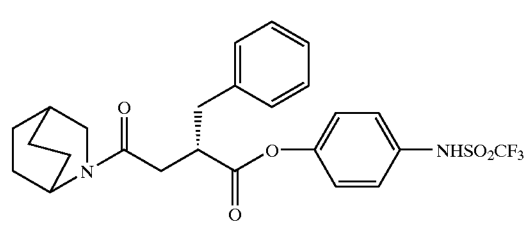 | 60–62 |

TABLE 6-continued
| No. | Structure | mp (° C.) |
|---|---|---|
| 29 | 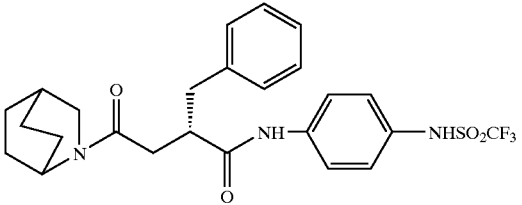 | 136–138 |
| 30 | 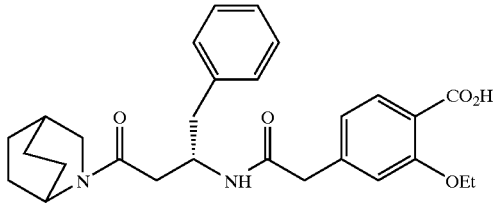 | 100–103 |
TABLE 7
| No. | Structure | mp (° C.) |
|---|---|---|
| 31 | 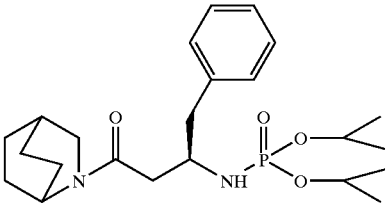 | oil |
| 32 | 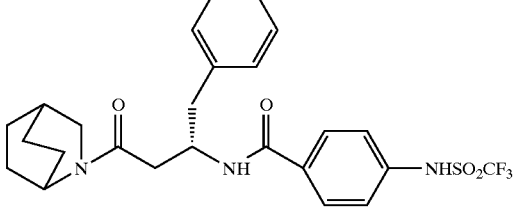 | oil |
| 33 | 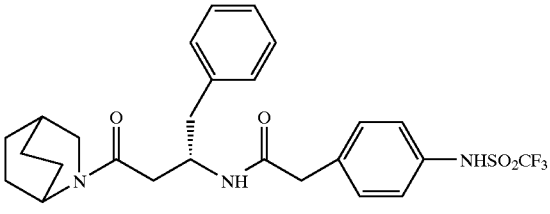 | 78–80 |
| 34 | 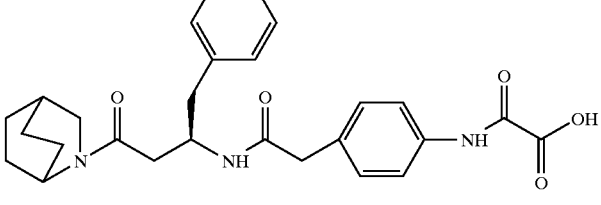 | 79–80 |

TABLE 7-continued

| No. | Structure | mp (° C.) |
|---|---|---|
| 35 | 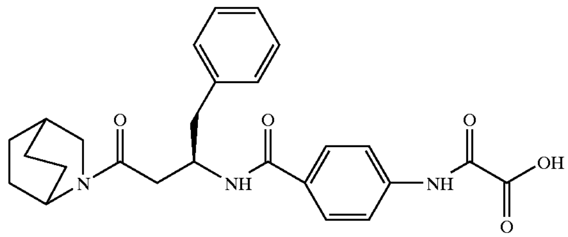 | 200–201 |

TABLE 8

| No. | Structure | mp (° C.) |
|---|---|---|
| 36 | 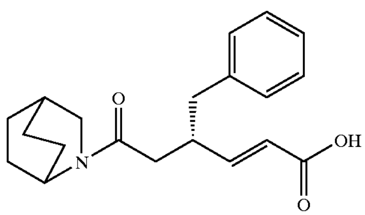 | 52–53 |
| 37 | 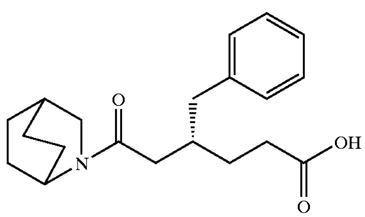 | 79–81 |
| 38 | 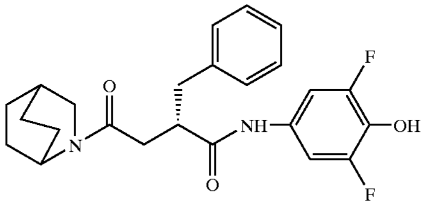 | 118–120 |
| 39 | 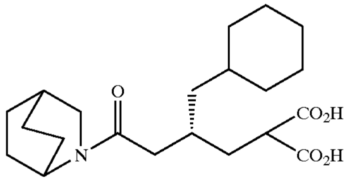 | 84–85 |
| 40 | 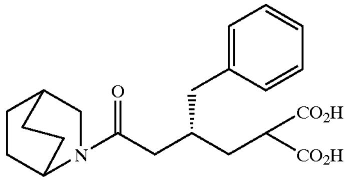 | 78–80 |

TABLE 9

| No. | Structure | mp (° C.) |
|---|---|---|
| 41 | 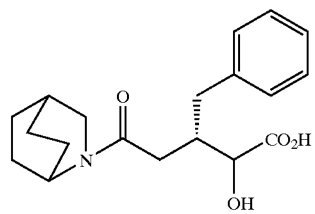 | 60–61 |
| 42 | 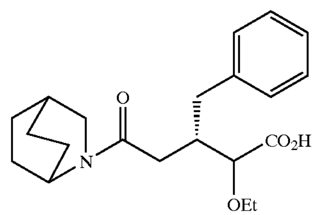 | oil |
| 43 | 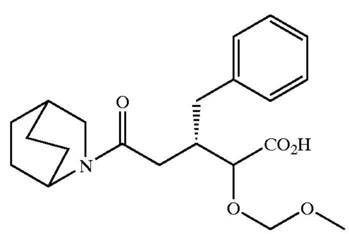 | oil |
| 44 | 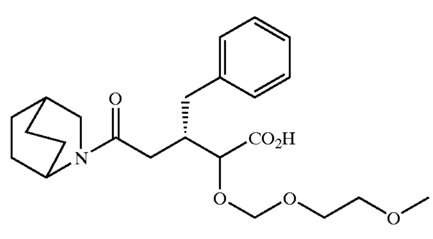 | oil |
| 45 | 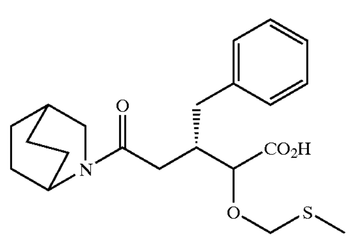 | oil |

TABLE 10

| No. | Structure | mp (° C.) |
|---|---|---|
| 46 | 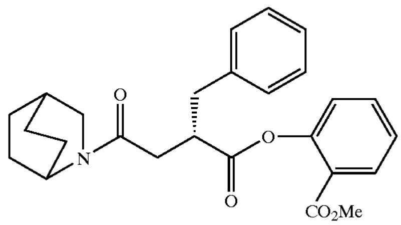 | oil |
| 47 | 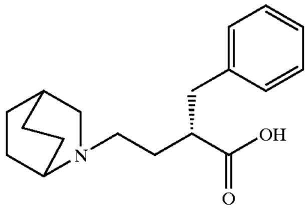 | 171–174 |
| 48 | 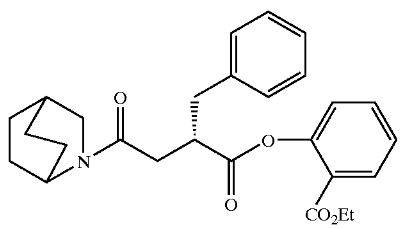 | oil |
| 49 | 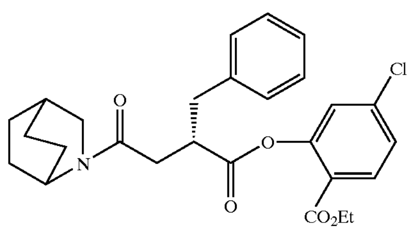 | oil |
| 50 | 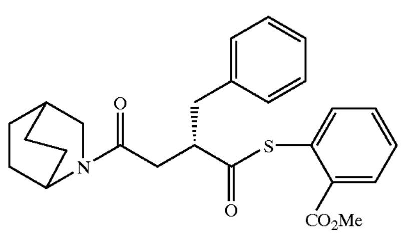 | oil |

TABLE 11

| No. | Structure | mp (° C.) |
|---|---|---|
| 51 | 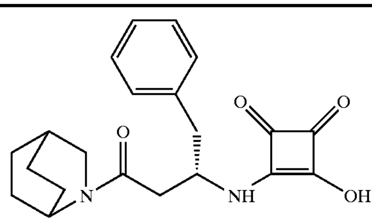 | 156–158 |
| 52 | 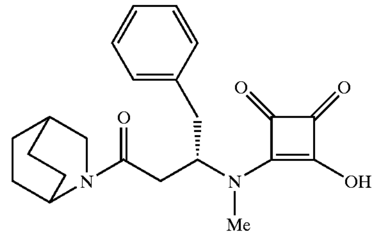 | 153–155 |
| 53 | 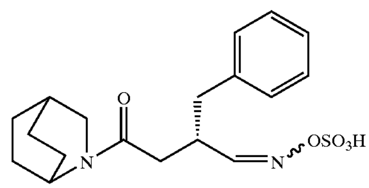 | 148–151 |

The compound of general formula (I) can be obtained as follows.

(A) In the compound of general formula (1), the compound of general formula (III) is prepared by the following reactions.

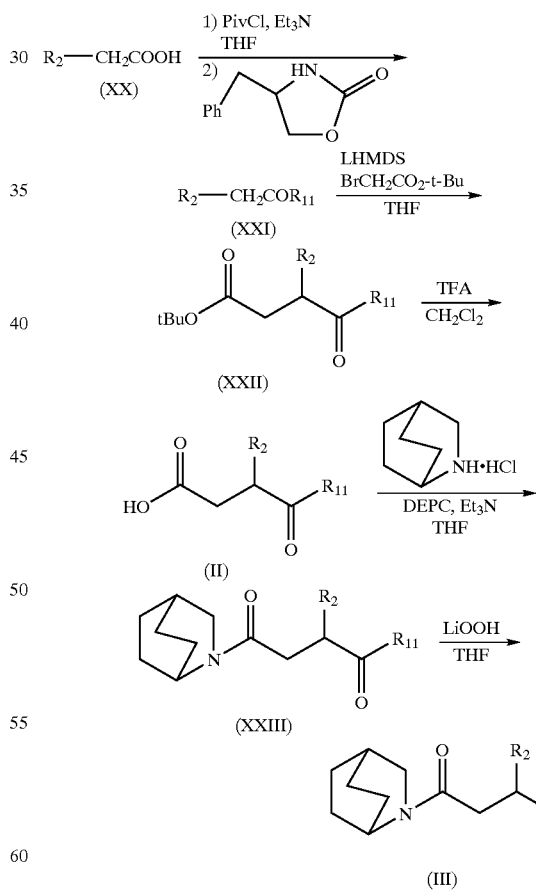

(wherein $R_2$ and $R_{11}$ are the same as mentioned above.)

The compound of general formula (XX) is reacted with PivCl (pivaloyl chloride) in the presence of organic base such as $Et_3N$ (triethylamine) or NMM (N-methylmorpholine) in THF to obtain a mixed anhydride, followed by the reaction with 4(S)— or 4(R)-benzyl-2-oxazolidinone in the presence of n-butyl lithium or LiCl to afford the compound of general formula (XXI). Subsequently, the compound of general formula (XXI) is converted to the compound of general formula (XXII) by an asynmmetric alhylation with the tert-butyl bromoacetate in THF using LHMDS (lithium hexamethyl disilazane) or LDA (lithium diisopropylamide) etc. Then the compound of general formula (II) is obtained by deprotection of the tert-butyl group using an acid such as TFA (trifluoroacetic acid) or HCl etc. in THF. Furthermore, the compound of general formula (XXIII) is obtained by the reaction with isoquinuclidine hydrochloride using a coupling reagent such as DEPC (diethylphosphoryl cyanide), DPPA (diphenylphosphorylazide), WSCDI (1-(3-dimethylarmrinopropyl)-3-ethylcarbodiimide. HCl salt), DCC (dicyclohexyl-carbodiimide) etc. in the presence of organic base such as $Et_3N$ or NMM etc. in THF or DMF. The chiral auxiliary (4-(S—) or 4-(R)-Benzyl-2-oxazolidinone) is removed by using of lithium hydroxide and hydrogene peroxide in THF to give the compound of general formula (III).

The compound of general formula (III) is also obtained by the same reaction using 1(S) or 1(R)-2, 10-camphersultam instead of 4(S) or 4(R)-benzyl-2-oxazolidinone.

(B) In the compound of general formula (I), the compound of general formula (VII) is prepared by the following reactions.

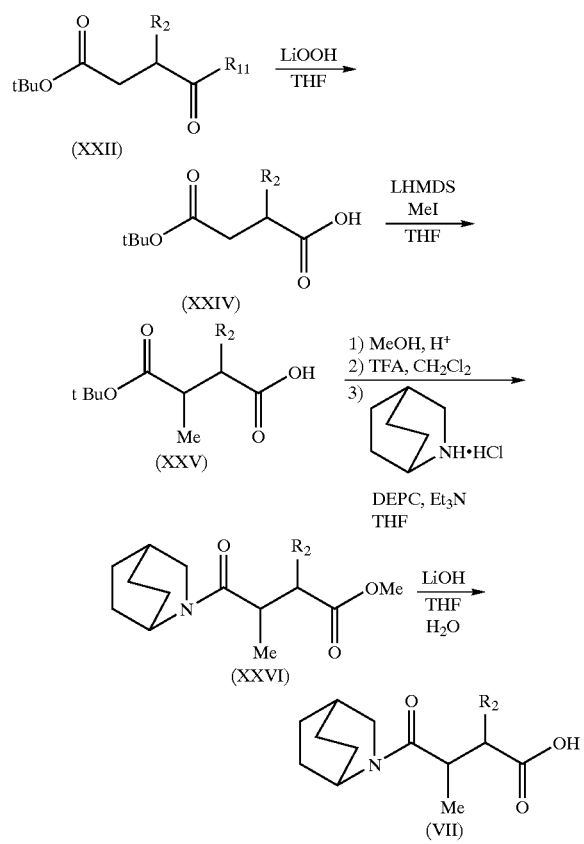

(wherein $R_2$ is the same as mentioned above.)

The chiral auxiliary of general formula (XXII) is removed to obtain the compound of general formula (XXIV). The obtained compound of general formula (XXIV) is reacted with methyl iodide using an base such as LHMDS, LDA etc. to afford the compound of general formula (XXV). Then, the compound of general formula (XXVI) is obtained by the esterification of the carboxylic acid group of general formula (XXV), followed by the deprotection of the tert-butyl group with acids such as HCl or TFA etc. and the condensation with isoquinuclidine hydrochloride. The obtained compound of general formula (XXV) is hydrolyzed by lithium hydroxide etc. in $THF/H_2O$ to give the compound of general formula (VII).

(C) In the compound of the general formula (I), the compound of general formula (V) is prepared by the following reactions.

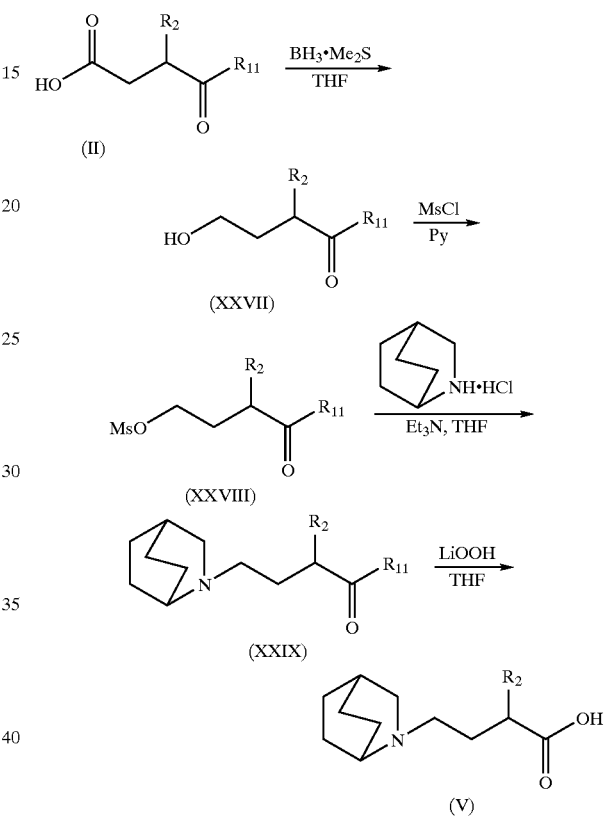

(wherein $R_2$ and $R_{11}$ are the same as mentioned above.)

The carboxylic acid group of general formula (II) is reduced with borane dimethylsulfide etc. to afford the compound of general formula (XXVII). Then, the compound of general formula (XXVII) is mesylated or tosylated to obtain the compound (XXVIII) with MsCl (methanesulfonyl chloride) or TsCl (p-toluenesulfonyl chloride) in the presence of base such as triethylamine, pyridine etc. in dichloromethane. The resulting compound (XXVIII) is reacted with isoquinuclidene hydrochloride in the presence of base such as triethylamine, potassium carbonate etc. in dichloromethane and DMF etc. and obtained the compound of general formula (XXIX). After removal of the chiral auxiliary in the compound (XXIX), the compound of general formula (V) was obtained.

The compound (XXIX) is also obtained by the chlorination of the compound (XXVII) with $PPh_3/CHBr_3$ or $SO_2Cl/C_6H_6$ and followed by the amination with isoquinuclidine.

(D) In the compound of the general formula (I), the compound of general formula (IX) is prepared by the following reactions.

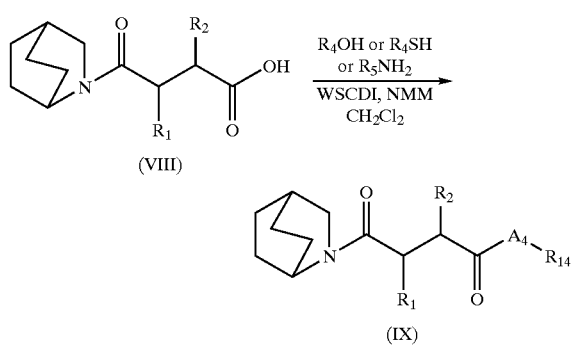

(VIII) → (IX)

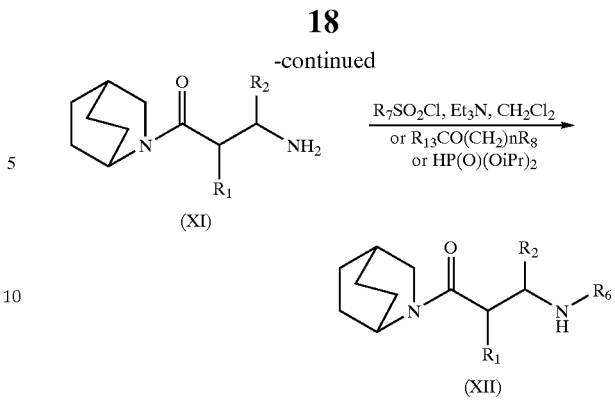

(XI) → (XII)

(wherein $R_1$, $R_2$, $R_4$, $R_5$ and $R_{14}$ are the same as mentioned above.)

The compound of general formula (IX) is obtained by the reaction with the compound of general formula (VIII) and $R_4OH$, $R_4SH$, or $R_5NH_2$ using the coupling agent such as DEPC, DPPA, WSCDI and DCC.

(E) In the compound of general formula (I), the compound of general formula (XII) is prepared by the following reactions.

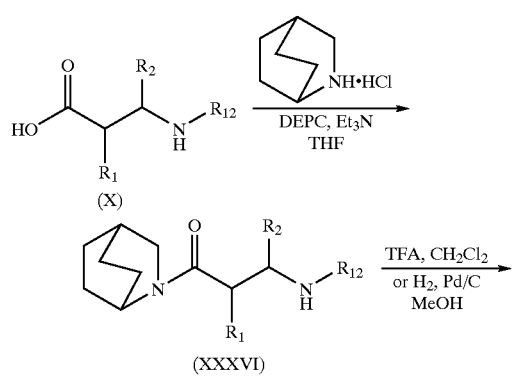

(X) → (XXXVI)

(wherein $R_1$, $R_2$, $R_6$, $R_7$, $R_8$, $R_{12}$ and $R_{13}$ are the same as mentioned above.)

The compound of general formula (X) is coupled with isoquinuclidine to afford the compound of general formula (XXXVI). In the case of that the protecting group of amine in the compound (XXXVI) is Boc group, the protecting group is removed by acid such as trifluoroacetic acid or HCl in dichloromethane or ethyl acetate to give the compound of general formula (XI). In the case of Cbz group, the protecting group is removed under hydrogene —Pd/C in methanol or THF etc. The obtained compound of general formula (XI) is reacted with sulfonyl chloride or acid chloride in the presence of base such as triethylamine, pyridine etc. in dichloromethane or DMF etc. or reacted with the ester compound ($R_3CO(CH_2)_nR_8$) in methanol or benzene etc. or reacted with diisopropylphosphate ($HP(O)(OiPr)_2$) in the presence of triethylamine in $CCl_4$ and obtained the compound of general formula (XII).

(F) In the compound of general formula (I), the compound of general formula (XIII) is prepared by the following reactions.

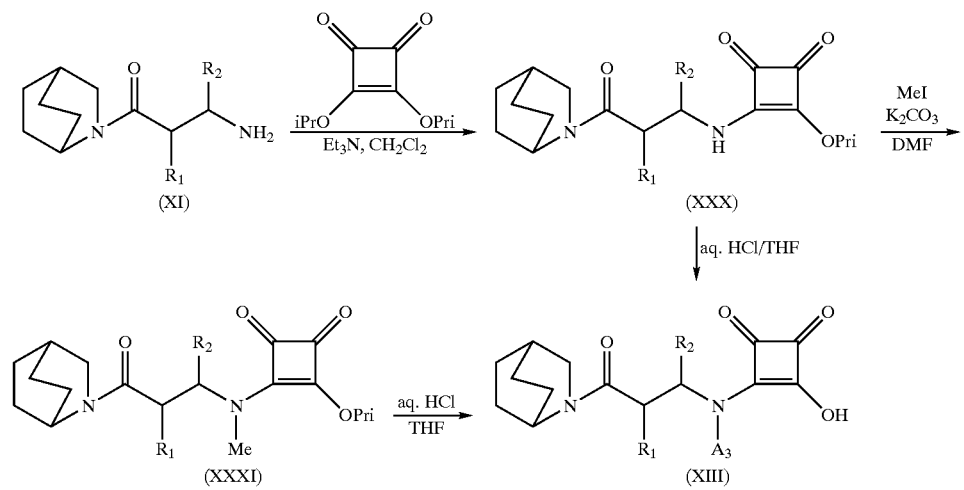

(XI) → (XXX) → (XXXI) → (XIII)

(wherein $R_1$, $R_2$ and $A_3$ are the same as mentioned above.)

The compound of general formula (XI) is reacetd with diisopropylsquarate in the presence of base such as triethylamine in dicholoromethane or THF etc. to obtain the compound of general formula (XXX), followed by the hydrolysis with aq. HCl in THF or benzene etc. to obtain the compound of general formula (XIII) (in the case of $A_3$ is hydrogen). The compound of general formula XIII, in the case of $A_3$ is methyl, is obtained by the reaction of the compound of general formula (XXX) with methyl iodide in the presence of base such as potassium carbonate in DMF or THF to afford the compound of general formula (XXI), followed by the hydrolysis to obtain the compound of general formula (XIII).

(G) In the compound of general formula (I), the compound of general formula (XVI) is prepared by the following reactions.

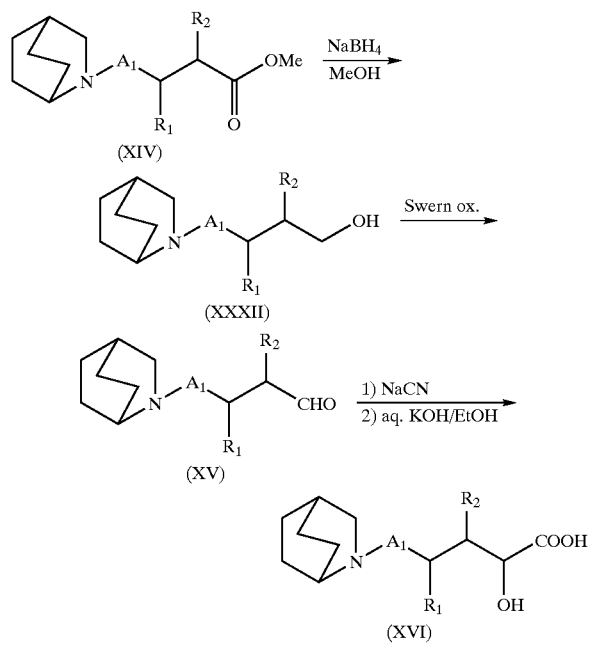

(wherein $R_1$, $R_2$ and $A_1$ are the same as mentioned above.)

The compound of general formula (XIV) is reduced by sodium borohydirde or lithium borohydride in methanol or THF etc. to give the compound of general formula (XXXII), following by the oxidation such as Swern oxidation etc. to yield the compound of general formula (XV). The resulting compound of general formula (XV) is converted to the cyanohydrine compound using potassium cyanide or sodium cyanide etc., followed by the hydrolysis with potassium hydroxide in ethanol to yield the compound of general formula (XVI).

(H) In the compound of general formula (I), the compound of general formula (XVII) is prepared by the following reactions.

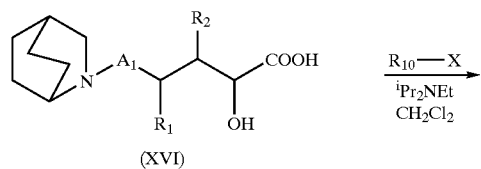

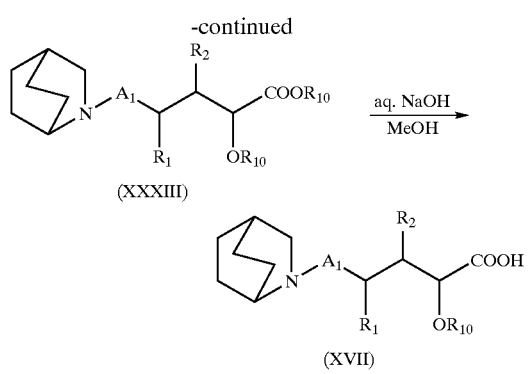

(wherein $A_1$, $R_1$, $R_2$, $R_{10}$ and X are the same as mentioned above.)

The compound of general formula (XVI) is reacted with $R_{10}$—X in the presence of base such as diisopropylethylamine or sodium hydride in dichloromethane or THF etc. to give the compound of general formula (XXXIII), followed by the hydrolysis using aq.NaOH in methanol or THF etc. to yield the compound of general formula (XVII).

(I) In the compound of general formula (I), the compound of general formula (XVIII) is prepared by the following reactions.

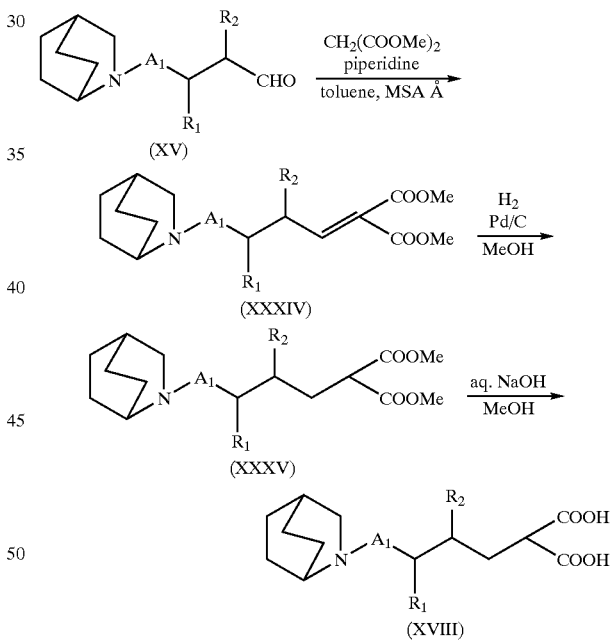

(wherein $A_1$, $R_1$ and $R_2$ are the same as mentioned above.)

The compound of general formula (XV) is subjected to Knoevenagel condensation using dimethyl malonate, followed by the hydrogenation of the obtained compound of general formula (XXXIV) to afford the compound of general formula (XXXV). Furthermore, the compound of general formula (XXXV) is hydrolyzed to obtain the compound of general formula (XVIII).

(J) In the compound of general formula (I), the compound of general formula (XIX) is prepared by the following reactions.

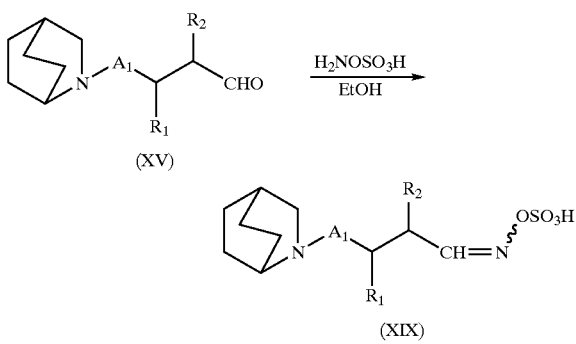

(wherein $A_1$, $R_1$ and $R_2$ are the same as mentioned above.)

The compound of general formula (XV) is reacted with hydroxylamine-o-sulfonic acid in ethanol or methanol or dichloromethane etc. to obtain the compound of general formula (XIX).

PHARMACOLOGICAL EXPERIMENT
Inhibition of Blood Glucose Increase in Normal Rats

Male Splague-Dawley rats (6 weeks old) were used. After 18 hr fasting, drugs dissolved or suspended in 0.5% methyl cellulose were orally administered simultaneously with glucose solution (2 g/kg). Blood was collected by tail snipping before and 1 hr after oral adminstration. Plasma glucose level was determined by the glucose oxidase method, using a commercially available kit (Glucose CII Test Wako, Wako, Osaka, Japan). The plasma glucose level after oral adminstration were compared with the level before oral administration and percent reduction of rised plasma glucose level relative to vehicle-treated group was calculated as follows:

Percent reduction (%)=($\Delta$Control–$\Delta$Treated)/($\Delta$Control)×100

$\Delta$control: rise in plasma glucose level observed 1 hr after oral administration in vehicle-treated group
$\Delta$Treated: rise in plasma glucose level observed 1 hr after oral administration in drug-treated group

| Compound No. | Dose (mg/kg) | Reduction percent (%) |
| --- | --- | --- |
| 1 | 10 | 35 |
| 10 | 10 | 45 |
| 11 | 10 | 43 |
| 14 | 30 | 32 |
| 15 | 10 | 35 |
| 17 | 10 | 48 |
| 18 | 10 | 82 |
| 45 | 10 | 59 |
| 46 | 10 | 88 |
| 47 | 10 | 26 |
| 48 | 10 | 55 |
| 50 | 10 | 66 |
| 52 | 10 | 31 |

EXAMPLE
The following Example are provided only for the purpose of the preparation of the compounds and not restricted the disclosed invention.

Reference 1
Synthesis of 4(R)-benzyl-3-N-(2-carboxymethyl-3-phenyl-propanoyl)-2-oxazolidione.

(a) Synthesis of 4(R)-benzyl-3-N-(3-phenylpropanoyl)-2-oxazolidinone.

To a solution of hydrocinnamic acid (10.2 g) and $Et_3N$ (10.2 mL) in THF (50 mL) at 0° C. under Ar was slowly added pivaloyl chloride (9.04 g) and allowed to stir at room temperature for 30 min to yield the mixanhydride solution. Separately in another flask, 4(R)-benzyl-2-oxazolidinone (10 g) was dissolved in THF (80 mL) and cooled to −78° C. under Ar and a 1.6M solution of n-butylithium in n-hexane (35.3 mL) was added to this solution and allowed to stir for 30 min. To this solution was added the previously prepared mixanhydride and the mixture was then allowed to stir for 3 h. The reaction mixture was poured into saturated $NH_4Cl$ solution (50 mL) and concentrated under reduced pressure. The residue was extracted with ethyl acetate (50 mL×3) and the ethyl acetate layer was washed with brine, dried over $Na_2SO_4$, filtered and concentrated in vacuo. The objective compound was obtained as a colorless crystal (13.1 g).

IR($cm^{-1}$):3022, 2944, 1785, 1602, 1374, 1203, 1113, 1047, 744, 696.

MS(m/z):309($m^+$), 133, 105, 84(BP), 65, 47.

$^1$H-NMR($CDCl_3$):2.75 (1H, dd), 3.03 (2H, m), 3.20–3.36 (3H, m), 4.17 (2H, m), 4.66 (1H, m), 7.16–7.34 (10H, m).

(b) Synthesis of 4(R)-benzyl-3-N-(2-tert-butyloxycarbonylmethyl-3-phenyl-propanoyl)-2-oxazolidione.

A 1.6M solution of n-butyllithium in n-hexane (11.2 mL) was added to a solution of diisopropylamine (2.72 mL) in THF (30 mL) at −78° C. After stirred for 30 min, the compound (5 g) obtained from the above mentioned step (a) was added, then tert-butyl bromoacetate was added and the reaction mixture was stirred for 30 min at −78° C., warmed to −20° C. over 1 h and then stirred for 1 h at 0° C. The reaction mixture was poured into saturated $NH_4Cl$ solution (50 mL) and extracted with ethyl acetate (50 mL×3). The ethyl acetate layer was washed with brine, dried ($Na_2SO_4$), filtered and concentrated in vacuo. The objective compound was obtained as a colorless crystal (4.01 g).

IR($cm^{-1}$):2968, 1782, 1695, 1356, 1290, 1149, 1053, 756, 699.

MS(m/z):423 ($m^+$−1), 367, 308, 178, 145, 117, 91, 57(BP).

$^1$H-NMR($CDCl_3$): 1.40 (9H, s), 2.37 (1H, dd), 2.64 (1H, dd), 2.73 (1H, dd), 2.85 (1H, dd), 3.01 (1H, dd), 3.31 (1H, dd), 3.93 (1H, t), 4.08 (1H, dd), 4.48–4.53 (2H, m), 7.21–7.36 (10H, m).

(c) Synthesis of 4(R)-benzyl-3-N-(2-carboxymethyl-3-phenylpropanoyl)-2-oxazolidinone.

The compound (2.0 g) obtained from the above mentioned step (b) was dissolved in $CH_2Cl_2$ (10 ML) and trifluoroacetic acid (3.6 mL) was added at 0° C. The mixture was stirred for 8 h at room temperature. The reaction mixture was poured into ice-water (50 mL) and extracted with $CHCl_3$ (20 mL×3). The $CHCl_3$ layer was washed with brine, dried ($Na_2SO_4$), filtered and concentrated in vacuo. The objective compound was obtained as a colorless crystal (1.72 g).

IR($cm^{-1}$):3016, 2914, 1776, 1701, 1389, 1206, 1110, 1005, 957, 699.

MS(m/z):367($m^+$), 190, 167, 147, 117, 91 (BP), 57.

$^1$H-NMR($CDCl_3$):2.48 (1H, dd), 2.64 (1H, dd), 2.74 (1H, dd), 2.97 (1H, dd), 3.04 (1H, dd), 3.24 (1H, dd), 3.97 (1H, t), 4.10 (1H, dd), 4.49–4.55 (2H, m), 7.22–7.34 (10H, m).

Reference 2
Synthesis of N-(2-tert-butyloxycarbonylmethyl-3-phenyl-propanoyl-(1S)-(−)-2,10-camphorsultam.

(a) Synthesis of N-(3-phenylpropanoyl)-(1S)-(−)-2,10-camphorsultam.

To a solution of (1S)-(−)-2,10-camphorsultam (1 g) in 15 mL of toluene was added 55% NaH (223 mg) at 0° C. After stirred for 30 min, hydrocinnamoyl chloride (0.83 mL) was added and the mixture was stirred for 2 h at room temperature. The reaction mixture was poured into saturated NH$_4$Cl solution (80 mL) and extracted with ethyl acetate (50 mL×3). The ethyl acetate layer was washed with brine, dried (Na$_2$SO$_4$), filtered and concentrated in vacuo.

The resulting product was purified by silica gel column chromatography using EtoAc:n-hexane (1:10). The objective compound was obtained as a colorless crystal (1.4 g).

IR(cm$^{-1}$):2944, 1677, 1452, 1320, 1218, 1134, 1113, 1065, 531.

MS(m/z):347(m$^+$), 240, 1.05(BP), 79, 55, $^1$H-NMR(CDCl$_3$):0.96 (3H, s), 1.09 (3H, s), 1.34–1.40 (2H, m), 1.85–1.91 (3H, m), 2.06 (2H, d), 2.99–3.08 (4H, m), 3.42 (1H, m), 3.48 (1H, m), 3.86 (1H, t), 7.18–7.29 (5H, m).

(b) Synthesis of N-(2-tert-butyloxycarbonylmethyl-3-phenylpropanoyl-(1S)-(−)-2,10-camphorsultam.

The compound (500 mg) prepared by the above mentioned step (a) was dissolved in THF (5 mL) and 1.6M solution of n-butyllithium in n-hexane (1.06 mL) was added at −78° C. and stirred for 30 min. Tert-butylbromoacetate (0.23 mL) and tetrabutylammonium iodide in HMPA (1 mL) was added to the mixture and the reaction mixture was stirred for 3 h at −78° C. The reaction mixture was poured into saturated NH$_4$Cl solution (50 mL) and extracted with ethyl acetate (50 mL×3). The ethyl acetate layer was washed with brine, dried (Na$_2$SO$_4$), filtered and concentrated in vacuo.

The resulting product was purified by silica gel column chromatography using EtoAc:n-hexane (1:2). The objective compound was obtained as a colorless crystal (525 mg).

IR(cm$^{-1}$):2962, 1725, 1677, 1326, 1284, 1152, 765, 531.

MS(m/z):461 (m$^+$), 405, 346, 256, 216(BP), 162, 115, 55.

$^1$H-NMR(CDCl$_3$):0.97 (3H, s), 1.25 (3H, s), 1.32–1.56 (2H, m), 1.38 (9H, s), 1.88 (3H, m), 2.03 (1H, dd), 2.15 (1H, m), 2.34 (1H, dd), 2.55 (1H, dd), 2.66 (1H, dd), 3.32 (1H, dd), 3.46 (1H, m), 3.53 (1H, m), 3.61 (1H, m), 3.92 (1H, dd), 7.19–7.30 (5H, m).

Example 1

Synthesis of (2S)-2-benzyl-4-(isoguinuclidin-2-yl)-4-oxo-butanoic acid (compound 1)

(a) Synthesis of 4(R)-benzyl-3-N-(2-isoguinuclidinecarbonylmethyl-3-phenyl-propanoyl)-2-oxazolidione.

The compound (500 mL) obtained from the above mentioned Reference 1 was dissolved in THF/DMF (3/1) (4 mL) and isoquinuclidin hydrochloride (241 mg), DEPC (0.166 mL) and Et$_3$N (0.57 mL) was added to this solution at 0° C. The mixture was stirred at room temperature for 30 min. The reaction mixture was poured into saturated NaHCO$_3$ (50 mL) and extracted with ethyl acetate (50 mL×3). The ethyl acetate layer was washed with saturated citric acid, brine, dried (Na$_2$SO$_4$), filtered and concentrated in vacuo. The objective compound was obtained a colorless crystal (269 mg).

IR(cm$^{-1}$):3412, 2988, 1766, 1636, 1440, 1378, 1252, 1196, 1004, 746, 508.

MS(m/z):460(m$^+$−1), 284, 256, 207, 178, 153, 117, 91 (BP), 55.

$^1$H-NMR(CDCl$_3$): 1.58–1.95 (9H, m), 2.34 and 2.41 (total 1H, each dd), 2.64–3.07 (4H, m), 3.28–3.46 (2H, m), 3.66 and 4.39 (total 1H, each s), 3.85 and 3.92 (total 1H, each t), 4.02–4.28 (2H, m), 4.47–4.66 (2H, m), 7.18–7.34 (10H, m).

(b) Synthesis of (2S)-2-benzyl-4-(isoquinuclidin-2-yl)-4-oxo-butanoic acid (compound 1).

The compound (143 mg) obtained from the above mentioned Example 1 (a) was dissolved in THF/DMF (3/1) (4 mL) and cooled to 0° C. and 30% H$_2$O$_2$ (0.16 mL) was added to the solution with stirring for 5 min. After addition of LiOH.H$_2$O (26 mg), the mixture was stirred for 2 h at room temperature, then 10% Na$_2$SO$_3$ (10 ML) was added drop wise. After stirring 15 min, the solvent was concentrated in vacuo.

The resulting residue was extracted with ethyl acetate (50 mL×3). The ethyl acetate layer was washed with brine, dried (Na$_2$SO$_4$), filtered and concentrated in vacuo. The resulting product was purified by silica gel column chromatography using CHCl$_3$:EtoAc (5:1). The objective compound was obtained as a colorless crystal (80 mg).

IR(cm$^{-1}$):2926, 2860, 1725, 1590, 1452, 1245, 1176, 732, 699.

MS(m/z):301(m$^+$), 257, 190, 153(BP), 117, 97, 82, 57.

$^1$H-NMR(CDCl$_3$): 1.54–1.85 (9H, m), 2.38 (1H, dd), 2.47 (1H, m), 2.76 (1H, m), 3.01 (1H, m), 3.11 (1H, m), 3.32 (1H, dd), 3.41 and 4.52 (total 2H, each s), 7.71–7.33 (5H, m), 13.18 (1H, br, s)

Example 2

Synthesis of (2S)-2-benzyl-4-(isoquinuclidin-2-yl)-4-oxo-butanoic acid phenylester (compound 15).

The compound (100 mg) obtained from the above mentioned Example 1 was dissolved in CH$_2$Cl$_2$ (5 mL) and phenol (94 mg), WSCDI (64 mg) dimethylaminopyridine (4 mg) was added to the solution at 0° C. The reaction mixture was stirred for 2 h at room temperature. The reaction mixture was poured into saturated citric acid (50 mL) and extracted with ethyl acetate (50 mL×3). The ethyl acetate layer was washed brine, dried (Na$_2$SO$_4$), filtered and concentrated in vacuo. The resulting product was purified by silica gel column chromatography using n-hexane:EtoAc (5:1). The objective compound was obtained as a colorless crystal (68 mg).

IR(cm$^{-1}$):3412, 2932, 1758, 1632, 1434, 1374, 1191, 1086, 921, 750.

MS(m/z):284(m$^+$−93,BP), 190, 153, 124, 95, 55.

$^1$H-NMR(CDCl$_3$):1.62–1.95 (9H, m), 2.40 and 2.48 (total 1H, each dd), 2.70–2.78 (total 1H, each dd), 2.98 (1H, m), 3.14 (1H, m), 3.32–3.50 (3H, m), 3.69 and 4.50 (total 1H, each s), 6.95–7.34 (10H, m).

Example 3

Synthesis of (2S)-2-benzyl-4-(isoquinuclidine-2-yl)-4-oxo-butanoic acid methyl ester (compound 13)

The compound (145 mg) obtained from the above mentioned Example 1 was dissolved in a mixture of MeOH (5 mL) and conc.H2SO$_4$ (1 mL) and the mixture was reflux for 1 h. The reaction mixture was concentrated in vacuo. The resulting product was poured into saturated NaHCO$_3$ (30 mL) and extracted with ethyl acetate (50 mL×3). The ethyl acetate layer was washed brine, dried (Na$_2$SO$_4$), filtered and concentrated in vacuo. The resulting product was purified by silica gel column chromatography using n-hexane:EtoAc (5:1). The objective compound was obtained as a colorless oil (149 mg).

IR(cm$^{-1}$):2926, 1728, 1626, 1434, 1371, 1164, 1098, 990, 747.

MS(m/z):315(m$^+$), 284, 173, 153, 117, 84(BP), 47.

$^1$H-NMR(CDCl$_3$):1.62–1.94 (9H, m), 2.24 and 2.32 (total 1H, each dd), 2.58–2.67 (total 1H, each dd), 2.81 (1H, m), 3.02 (1H, m), 3.24–3.42 (3H, m), 3.65 and 3.66 (total 3H, each s), 3.66 and 4.46 (total 1H, each m), 7.15–7.30 (5H, m).

Example 4
Synthesis of N-[(2S)-2-benzyl-4-(isoquinuclidine-2-yl)-4-oxo-butanoyl]4-aminopyridine (compound 2).

The compound (87 mg) obtained from the above mentioned Example 1 was dissolved in $CH_2Cl_2$ (3 mL) and HOBt (53 mg), WSCDI (67 mg) and N-methylmorpholine (0.04 mL) was added to the solution at 0° C. The mixture was stirred for 1 h at room temperature, N-methylmorpholine (0.05 mL) and 4-methylaminopyridine (41 mg) was added to the mixture. The reaction mixture was stirred for 8 h at room temperature. The reaction mixture was poured into saturated NaCl (50 mL) and extracted with ethyl acetate (50 mL×3). The ethyl acetate layer was washed brine, dried ($Na_2SO_4$), filtered and concentrated in vacuo. The resulting product was purified by silica gel column chromatography using $CHCl_3$:MeOH (50:1). The objective compound was obtained as a colorless crystal (10 mg).

IR($cm^{-1}$):3400, 2926, 1692, 1605, 1527, 1455, 1170, 966, 822, 750.

MS(m/z):377($m^+$), 284, 256, 225, 190, 153, 119, 91, 71, 52(BP).

$^1$H-NMR($CDCl_3$): 1.58–1.71 (8H, m), 1.93 (1H, s), 2.35 (1H, ddd), 2.71–2.86 (2H, m), 3.07 (1H, m), 3.23 (1H, m), 3.31–3.49 (2H, m), 3.76 and 4.38 (total 1H, each s), 7.17–7.36 (5H, m), 7.49 (2H, d), 7.66 and 7.77 (total 1H, each d), 8.33 (2H, d).

Example 5
Synthesis of S-(o-methoxycarbonyl)phenyl (2S)-2-benzyl-4-(isoquinuclidine-2-yl)-4-oxothiobutanoate (compound 50).

The compound (200 mg) obtained from the above mentioned Example 1 was dissolved in $CH_2Cl_2$ (3 mL) and o-methoxycarbonyl-thiophenol (167 mg), WSCDI (191 mg) and dimethylamino-pyridine (16 mg) was added to the solution at 0° C. The mixture was stirred at room temperature for 3 h and the reaction mixture was poured into saturated $NH_4Cl$ (50 mL) and extracted with ethyl acetate (50 mL×3). The ethyl acetate layer was washed brine, dried ($Na_2SO_4$), filtered and concentrated in vacuo. The resulting product was purified by silica gel column chromatography using $CHCl_3$:MeOH (20:1). The objective compound was obtained as a yellow oil (132 mg).

IR($cm^{-1}$):2926, 1725, 1632, 1440, 1290, 1254, 933, 747, 699.

ESI-MS:($m^+H$)+m/z 284.

$^1$H-NMR($CDCl_3$): 1.53–1.93 (9H, m), 2.32 (1H, m), 2.66–2.86 (2H, m), 3.15–3.39 (3.5H, m), 3.65 (1H, m), 3.85 (3H, s), 4.47 (0.5H, s), 7.15–7.90 (9H, m).

Example 6
Synthesis of o-ethoxycarbonylphenyl (2S)-2-benzyl-4-(isoquinuclidine-2-yl)-4-oxo-butanoate (compound 48)

It was prepared following the Example 2, starting from the compound (200 mg) obtained from the above mentioned Example 1 and ethyl salicylate (0.1 mL). The resulting product was purified by silica gel column chromatography using n-hexane: EtoAc (2:1). The objective compound was obtained as a colorless oil (250 mg).

IR($cm^{-1}$):2926, 1722, 1626, 1443, 1293, 1254, 1134, 1080, 750.

MS(m/z):450($m^+$), 284, 190, 153, 120(BP), 92, 65.

$^1$H-NMR($CDCl_3$): 10.35 (3H, m), 1.59–1.95 (9H, m), 2.43 (1H, m), 2.67 (1H, m), 2.99 (1H, m), 3.28–3.44 (3H, m), 3.54 (1H, m), 3.69 and 4.51 (total 1H, each s), 4.31 (2H, m), 7.09 (1H, m), 7.21–7.34 (6H, m), 7.51 (1H, m), 7.96 (1H, m)

Example 7
Synthesis of o-methoxycarbonylphenyl (2S)-2-benzyl-4-(isoquinuclidine-2-yl)-4-oxo-butanoate (compound 46)

The compound (180 mg) obtained from the above mentioned Example 2 was reacted with methyl salicylate (0.08 mL) by the same procedure described in Example 1.

The resulting product was purified by silica gel column chromatography using n-hexane: EtoAc (2:1). The objective compound was obtained as a colorless oil (220 mg).

IR($cm^{-1}$):2932, 172, 1629, 1437, 1296, 1257, 1134, 1083, 747.

MS(m/z):435($m^+$), 284, 242, 192, 153(BP), 120, 91, 55.

$^1$H-NMR($CDCl_3$): 1.62–1.94 (9H, m), 2.41 (1H, m), 2.76 (1H, m), 2.98 (1H, m), 3.28–3.44 (3H, m), 3.56 (1H, m), 3.69 and 4.50 (total 1H, each s), 3.83 (3H, m), 7.08 (1H, m), 7.22–7.34 (6H, m), 7.52 (1H, t), 7.97 (1H, d).

Example 8
Synthesis of p-methoxyphenyl (2S)-2-benzyl-4-(isoquinuclidine-2-yl)-4-oxo-butylate (compound 17).

The compound (1.0 g) obtained from the above mentioned Example 2 was reacted with p-methoxy phenol by the same procedure described in Example 1 (1.24 g).

The resulting product was purified by silica gel column chromatography using n-hexane: EtoAc (2:1). The objective compound was obtained as a colorless oil (1.21 g)

IR($cm^{-1}$):2932, 1746, 1626, 1440, 1299, 1248, 1137, 1029, 750.

MS(m/z):408($m^+$+1), 284(BP), 256, 190, 145, 117, 91, 55.

$^1$H-NMR($CDCl_3$):1.60–1.95 (9H, m), 2.39 and 2.46 (total 1H, each dd), 2.73 (1H, m), 2.97 (1H, m), 3.12 (1H, m), 3.40 (3H, m), 3.69 and 4.49 (total 1H, each s), 3.77 (3H, s), 6.85 (4H, m), 7.29 (10H, m).

Example 9
Synthesis of p-hydroxy phenyl (2S)-2-benzyl-4-(isoquinuclidine-2-yl)-4-oxo-butyrate (compound 18)

The compound (300 mg) obtained from the above mentioned Example 2 was reacted with p-benzyloxyphenol (598 mg) by the same procedure described in Example 1. The resulting product was dissolved in THF (5 mL) and 5% Pd on carbon (100 mg) was added. The reaction mixture was stirred for 5 h under a hydrogen atmosphere, filtered and concentrated in vacuo. The resulting product was purified by silica gel column chromatography using n-hexane:EtoAc (2:1). The objective compound was obtained as a colorless oil (350 mg).

IR($cm^{-1}$):3266, 2938, 1749, 1605, 1446, 1374, 1245, 1188, 1002, 774.

MS(m/z):393($m^+$), 258, 187, 149(BP), 125, 86, 47.

$^1$H-NMR($CDCl_3$): 1.61–1.95 (9H, m), 2.40 (1H, m), 2.75 (1H, m), 2.94 (1H, m), 3.17 (1H, m), 3.29 (3H, m), 3.69 and 4.46 (total 1H, each s), 6.73 (4H, m), 7.28 (10H, m).

Reference 3
Synthesis of (2S)-2-benzyl-4(isoquinuclidine-2-yl)-4-oxo-butanal.

(a) Synthesis of (2S)-2-benzyl-4-(isoquinuclidine-2-yl)-4-oxo-butanol.

The compound (1.08 g) obtained from the above mentioned Example 3 was dissolved in Ether/THF (10:1) (11 mL) and $LiBH_4$ (75 mg) was added to the solution at 0° C. After stirred for 30 min at 0° C., the reaction mixture was poured into 10% HCl (30 mL) and extracted with ethyl acetate (50 mL×3). The ethyl acetate layer was washed with brine, dried ($Na_2SO_4$), filtered and concentrated in vacuo. The resulting product was purified by silica gel column chromatography using CHCl$_3$:MeOH (20:1). The objective compound was obtained as a colorless crystal (778 mg).

IR(cm$^{1-}$): 3376, 2926, 2860, 1605, 1449, 1248, 1032, 741, 699.

MS(m/z):287(m$^+$), 262, 153, 118, 83(BP), 47.

$^1$H-NMR(CDCl$_3$): 1.55–1.94 (9H, m), 2.26–2.45 (3H, m), 2.54 (1H, m), 2.75 (1H, m), 3.21 (1H, m), 3.39 (1H, s), 3.47 and 4.50 (total 1H, each s), 3.54 (1H, m), 3.72 (1H, m), 7.17–7.30 (5H, m).

(b) Synthesis of (2S)-2-benzyl-4-(isoquinuclidine-2-yl)-4-oxo-butanal.

Oxalyl chloride (2M, CH$_2$Cl$_2$, 1.9 mL) was dissolved in CH$_2$CL2 (3 mL) at –60° C. under Ar and DMSO (0.6 mL) was added to the solution. After stirred for 20 min, the compound (587 mg) obtained from the above mentioned Example 3 (a) in CH$_2$Cl$_2$ (7 mL) was added to the mixture. After stirred for 1.5 h, NEt$_3$ (1.7 mL) was added and allowed the stir for 1 h. The reaction mixture was poured into H$_2$O (50 mL) and extracted with ether (500 mL×3). Ether layer was washed with brine, dried (Na$_2$SO$_4$), filtered and concentrated in vacuo. The resulting product was purified by silica gel column chromatography using ether. The objective compound was obtained as a yellow oil (580 mg).

IR(cm$^{-1}$):2926, 2854, 1722, 1626, 1440, 1248, 738, 699.

MS(m/z):285(m$^+$), 153, 124, 86(BP), 58.

$^1$H-NMR(CDCl$_3$): 1.58–1.95 (9H, m), 2.34 (1H, m), 2.61 (1H, m), 2.79 (1H, m), 3.11 (1H, m), 3.24 (1H, m), 3.41 (1H, m), 3.64 and 4.46 (total 1H, each s), 7.17–7.32 (5H, m), 9.88 (1H, d).

Example 10

Synthesis of (4S)-4-benzyl-2-carboxy-6-(isoquinuclidine-2-yl)-6-oxo-2-hexanoic acid (compound 40).

(a) Synthesis of (4S)4-benzyl-2-methoxycarbonyl-6-(isoquinuclidine-2-yl)-6-oxo-hexen Acid.

The compound (100 mg) obtained from the above mentioned Example 2 was dissolved in tolune:cyclohexane (1:1) (4 mL) and diethylmalonate (0.048 mL), benzoic acid (1.5 mg), piperidine (0.002 mL) and MS 4 Å (50 mg) were added to the solution. The mixture was refluxed for 6 h and poured into saturated citric acid (50 mL) and extracted with ethyl acetate. The ethyl acetate layer was washed with saturated NaHCO$_3$ and brine, dried (Na$_2$SO$_4$), filtered and concentrated in vacuo. The resulting product was purified by silica gel column chromatography using EtoAc:n-hexane (1:2). The objective compound was obtained as a yellow oil (128 mg).

IR(cm$^{-1}$):2926, 1740, 1629, 1440, 1248, 1011, 747.

MS(m/z):399(m$^+$), 335, 268, 185, 153, 124, 95(BP), 59.

$^1$H-NMR(CDCl$_3$): 1.54–1.94 (9H, m), 2.32 (1H, m), 2.80–3.59 (5H, m), 3.75 (6H, m), 4.37–4.53 (2H, m), 5.68–5.89 (1H, m), 6.99–7.29 (5H, m).

(b) Synthesis of (4S)-4-benzyl-2-methoxycarbonyl-6-(isoquinuclidine-2-yl)-6-oxo-2-hexanoic Acid Methyl Ester.

A mixture of the compound (128 mg) obtained from the above mentioned Example 10 (a) in MeOH (5 mL) and 10% Pd on carbon (50 mg) was stirred for 12 h under a hydrogen atmosphere, filtered and concentrated in vacuo. The objective compound was obtained as a colorless oil (128 mg).

IR(cm$^{-1}$):2932, 1734, 1629, 1437, 1248, 1002, 744.

MS(m/z):401 (m$^+$), 370, 227, 153(BP), 124, 82, 54.

$^1$H-NMR(CDCl$_3$): 1.62–2.19 (12H, m), 2.68 (4H, m), 3.37–3.59 (3.5H, m), 3.72 (6H, m), 4.51 (0.5H, m), 7.01–7.29 (5H, m).

(c) Synthesis of (4S)-4-benzyl-2-carboxy-6-(isoquinuclidine-2-yl)-6-oxo-2-hexanoic acid (compound 40).

To a solution the compound (128 mg) obtained from the above mentioned Example 10 (b) in MeOH:THF (2:1) (3 mL) was added 10% NaOH (1 mL) at 0° C. The mixture was stirred for 3 h at room temperature and treated with saturated citric acid to adjust the pH 7. The reaction mixture was extracted with CHCl$_3$ (50 mL×3). The CHCl$_3$ layer was washed with brine, dried (Na$_2$SO$_4$), filtered and concentrated in vacuo. The objective compound was obtained as a colorless crystal (96 mg).

IR(cm$^{-1}$):3406, 2932, 1707, 1563, 1455, 1212, 744.

ESI-MS:(m+H)+m/z 374

$^1$H-NMR(CDCl$_3$): 1.55–1.98 (10H, m), 2.04–2.38 (2H, m), 2.48–2.61 (3H, m), 2.78 (1H, m), 3.08 and 3.33 (total 1H, each d), 3.39 (2H, m), 3.56 and 4.50 (total 1H, each s), 7.12–7.33 (5H, m).

Example 11

Synthesis of N-(3-hydroxy-3-cyclobutene-1,2-dione-4-yl)-(1S)-[2-(isoquinuclidine-2-yl)-2-oxo-ethyl]phenyl ethylamine (compound 51).

(a) Synthesis of N-(3-isopropoxy-3-cyclobutene-1,2-dione-4-yl)-(1S)-[2-(isoquinuclidine-2-yl)-2-oxo-ethyl] phenyl ethylamine To a solution of (1S)-[2-(isoquinuclidine-2-yl)-2-oxo-ethyl]phenyl amine (600 mg) in CH$_2$Cl$_2$ (8 mL) were added Et$_3$N (0.37 mL) and Diisopropyl squarate (437 mg). The reaction mixture was refluxed for 6 h, poured into H$_2$O (50 mL) and extracted with ethyl acetate (50 mL×3). The ethyl acetate layer was washed with brine, dried (Na$_2$SO$_4$), filtered and concentrated in vacuo. The resulting product was purified by silica gel column chromatography using CHCl$_3$:EtoAc (1:1). The objective compound was obtained as a colorless oil (903 mg).

IR(cm$^{-1}$):2908, 1803, 1710, 1557, 1377, 1239, 1086, 765.

MS(m/z):410(m$^+$), 319, 283, 256, 213, 181, 138(BP), 95, 67.

$^1$H-NMR(CDCl$_3$):1.40 (6H, d), 1.54–2.02 (9H, m), 2.43 and 2.53 (total 2H, each m), 2.95–3.25 (3H, m), 3.46 and 4.53 (total 1H, each s), 3.47 (1H, m), 4.24 and 4.71 (total 1H, each m), 5.34 (1H, m), 7.16–7.31 (5H, m), 7.42 and 7.52 (total 1H, each m).

(b) Synthesis of N-(3-hydroxy-3-cyclobutene-1,2-dione-4-yl)-(1S)-[2-(isoquinuclidine-2-yl)-2-oxo-ethyl]phenyl ethylamine (compound 51).

A mixture of the compound (450 mg) obtained from the above mentioned procedure Example 11 (a) in THF (20 mL) and 10% HCl (5 mL) was refluxed for 12 h. The reaction mixture was treated with 10% NaOH to adjust the pH 10 and was washed with ethyl acetate. The basic layer was treated with 10% HCl to adjust the ph7 and extracted with CHCl$_3$ (50 mL×3). The CHCl$_3$ layer was washed with brine and dried (Na$_2$SO$_4$), filtered and concentrated in vacuo. The resulting product was purified by silica gel column chromatography using CHCl$_3$:MeOH (10:1). The objective compound was obtained as a colorless crystal (342 mg).

IR(cm$^{-1}$):3244, 2926, 1800, 1584, 1422, 1245, 744.

ESI-MS:(m$^+$H)$^+$m/z 369.

$^1$H-NMR(CDCl$_3$): 1.67–2.02 (9H, m), 2.53 (1H, d), 2.61 (1H, d), 2.96–3.47 (4H, m), 3.54 and 4.44 (total 1H, each s), 4.68 (1H, m), 7.19–7.32 (5H, m), 8.24 (1H, m).

Example 12

Synthesis of N-(3-hydroxy-3-cyclobutene-1,2-dione-4-yl)-N-methyl-(1S)-[2-(isoquinuclidin-2-yl)-2-oxo-ethyl]-phenyl ethylamine. (compound 52)

(a) Synthesis of N-(isopropoxy-3-cyclobutene-1,2-dione-4-yl)-N-methyl-(1S)-[2-(isoquinuclidin-2-yl)-2-oxo-ethyl] phenyl ethylamine.

A mixture of the compound (500 mg) obtained from the above mentioned Example 11 (a) was dissolved in DMF (15 mL) and CH$_3$I (0.1 mL), K$_2$CO$_3$ (168 mg) was added. The mixture was stirred at room temperature for 12 h. The reaction mixture was poured into H$_2$O (50 mL) and extracted with ethyl acetate (50 mL×3), the ethyl acetate layer was washed with brine, dried (Na$_2$SO$_4$), filtered and concentrated in vacuo. The objective compound was obtained as a yellow oil (430 mg).

IR(cm$^{-1}$):2926, 1794, 1698, 1590, 1449, 1386, 1095, 747.
MS(m/z):424(m$^+$), 333, 291, 256, 230, 195(BP), 95, 55.
$^1$H-NMR(CDCl$_3$): 1.36–1.48 (6H, m), 1.59–1.99 (9H, m), 2.50–3.05 (4H, m), 3.05 and 3.24 (total 3H, each d), 3.43 (2H, m), 3.66 and 4.46 (total 1H, each m), 4.63 (1H, m), 5.40 (1H, m), 7.16–7.32 (5H, m).

(b) Synthesis of N-(3-hydroxy-3-cyclobutene-1,2-dione-4-yl)-N-methyl-(1S)-[2-(isoquinuclidine-2yl)-2-oxo-ethyl] phenyl ethylamine (compound 52)

A mixture of the compound (430 mg) obtained from the above mentioned Example 12 (a) in THF (5 mL) and 10% HCl (5 mL) was refluxed for 3 h. The reaction mixture was poured into H$_2$O (50 mL) and extracted with CHCl$_3$.(50 mg×3) the CHCl$_3$ layer was washed with brine, dried (Na$_2$SO$_4$), filtered and concentrated in vacuo. The resulting product was purified by silica gel column chromatography using CHCl$_3$:MeOH (10:1). The objective compound was obtained as a colorless crystal (386 mg).

IR(cm$^{-1}$):3406, 2926, 1797, 1578, 1452, 1245, 699.
ESI-MS:(m+H)$^+$m/z 383.
$^1$H-NMR(CDCl$_3$): 1.64–1.96 (9H, m), 2.63 (1H, m), 2.83–3.08 (3H, m), 3.22 (3H, d), 3.40 (2H, m), 3.67 and 4.45 (total 1H, each s), 4.68 (1H, m), 5.98 (1H, s), 7.19–7.32 (5H, m).

Example 13

Synthesis of 4-(isoquinuclidin-2-yl)-4-oxo-(2S)-benzyl-butylaldehydeoxime-o-sulfonic acid (compound 53)

Hydroxylamine-o-sulfonic acid (333 mg) was added at room temperature of to a solution the compound (700 mg) obtained from the above mentioned Reference 2 in EtOH (10 mL) and stirred for 3 h. The solvent was concentrated in vacuo. The objective compound was obtained as a colorless crystal (275 mg).

IR(cm$^{-1}$):3418, 3100, 1665, 1440, 1398, 1206, 1047, 624.
ESI-MS:(m+H)$^+$m/z 381
$^1$H-NMR(DMSO): 1.66–1.98 (9H, m), 2.32–2.62 (2H, m), 2.85–3.00 (2H, m), 3.10–3.22 (1H, m), 3.33–3.59 (2H, m), 3.80 and 4.40 (total 1H, each m), 6.98 and 7.56 (total 1H, each m), 7.30–7.42 (5H, m), 9.40 (1H, s).

Example 14

Synthesis of (1S)-[2-(isoquinuclidin-2-yl)-2-oxo-ethyl]-N-trifluoromethanesulfonyl-phenylethyl amine (compound 16)

(1S)-[2-(isoquinuclidin-2-yl)-2-oxo-ethyl]-phenyl ethylamine (300 mg) was dissolved in CH$_2$Cl$_2$ (5 mL) and then Et$_3$N (0.23 mL), trifluoromethansulfonic anhydride (0.28 mL) was added at −78° C. After stirring 2 h, MeOH (1 mL) and 10% NaOH (0.3 mL) was added and stirred for 10 min. The reaction mixture was poured into H$_2$O (50 mL) and extracted with ethyl acetate (50 mL×3), the ethyl acetate layer was washed with brine, dried (Na$_2$SO$_4$), filtered and concentrated in vacuo. The resulting product was purified by silica gel column chromatography using EtoAc:n-hexane (1:1). The objective compound was obtained as a colorless crystal (115 mg).

IR(cm$^{-1}$):3052, 2938, 1602, 1461, 1374, 1230, 1071, 750.
MS(m/z):404(m$^+$), 313, 255, 138(BP), 91, 55.
$^1$H-NMR(CDCl$_3$): 1.58–1.90 (9H, m), 2.30 (1H, d), 2.41 (1H, d), 2.94–3.21 (3H, m), 3.41 and 4.54 (total 1H, each s), 3.46 (1H, m), 3.94–4.01 (1H, m), 7.13–7.33 (5H, m), 7.56 and 7.71 (total 1H, each d).

Example 15

Synthesis of N-[(2S)-benzyl-4-(isoquinuclidine-2-yl)-4-oxo-butanoyl]-(3,5-difluoro-4-hydroxy) aniline (compound 38)

Oxalyl chloride (2M CH$_2$Cl$_2$) (0.38 mL) was dissolved in CH$_2$Cl (2 mL)/DMF (0.07 mL) at −15° C. and stirred for 30 min. The mixture was concentrated in vacuo and CH$_2$Cl$_2$ (2 mL) was added at 0° C. The compound (200 mg) obtained from the above mentioned Example 1 was slowly added to it and the mixture was stirred for 30 min. In a separate flask, 3,5-difluoro-4-hydroxyaniline. HCl (241 mg) was dissolved in CH$_2$Cl$_2$ (4 mL) and then Et$_3$N (0.42 mL) was added at 0° C. After stirring 15 min, above the reaction mixture was added to this solution at 0° C. over 5 min. The mixture was then allowed to stir for 30 min. The reaction mixture was poured into H$_2$O (50 mL) and extracted with ethyl acetate. The organic layer was washed with brine, dried (Na$_2$SO$_4$), filtered and concentrated in vacuo. The resulting product was purified by silica gel column chromatography using CHCl$_3$:MeOH (5:1). The objective compound was obtained as a yellow crystal (100 mg).

IR(cm$^{-1}$):3280, 2932, 1611, 1437, 1350, 1236, 1017, 699.
MS(m/z):428(m$^+$), 284, 190, 145, 111, 84, 57(BP).
$^1$H-NMR(CDCl$_3$): 1.55–1.93 (9H, m), 2.36 (1H, m), 2.77 (2H, m), 3.10–3.42 (4H, m), 3.68 and 4.44 (total 1H, each s), 6.26 (1H, s), 7.00 (2H, m), 7.16–7.27 (5H, m), 8.80 and 8.95 (total 1H, each s).

Example 16

Synthesis of N-Diisopropoxyphosphoryl-(1S)-[2-(isoquinuclidin-2-yl)-2-oxo-ethyl]-phenylethylamine (compound 31)

To a solution of (1S)-[2-(isoquinuclidine-2-yl)-2-oxo-ethyl]phenyl amine (300 mg) in CCl$_4$ (3.5 mL) were added Et$_3$N (0.31 mL) and diisopropyl phosphate (0.13 mL) at 0° C. After stirring 12 h, the reaction mixture was poured into H$_2$O (50 mL) and extracted with ethyl acetate (50 mL×3). The resulting product was purified by silica gel column chromatography using CHCl$_3$:MeOH (50:1). The objective compound was obtained as a colorless oil (360 mg).

IR(cm$^{-1}$):3208, 2920, 1626, 1422, 1383, 1245, 1101, 744.
MS(m/z):436(m$^+$), 345, 261, 138(BP), 91, 47.
$^1$H-NMR(CDCl$_3$): 1.23–1.39 (12H, m), 1.63–2.00 (9H, m), 2.28 (1H, d), 2.38 (1H, d), 2.94–3.22 (3H, m), 3.43 (1H, m), 3.54 and 4.55 (total 1H, each s), 3.77 (1H, m), 4.06 and 4.78 (total 1H, each m), 7.18–7.29 (5H, m).

Example 17

Synthesis of N-Carboxymethylsulfonyl-(1S)-[2-(isoquinuclidin-2-yl)-2-oxo-ethyl]phenyl ethylamine (compound 20)

(a) Synthesis of N-ethoxycarbonylmethylslufonyl-(1S)-[2-(isoquinuclidin-2-yl)-2-oxo-ethyl]phenyl ethylamine A mixture of (1S)-[2-(isoquinuclidin-2-yl)-2-oxo-ethyl] phenyl ethylamine (300 mg) and Et$_3$N (0.92 mL) in CH$_2$Cl$_2$ (2 mL) was cooled to 0° C. and chrolosulfonylacetic acid ethyl ester (494 mL) was slowly added to the mixture. After stirring 4 h, the reaction mixture was poured into saturated NH$_4$Cl (50 mL) and extracted with ethyl acetate (50 mL×3). The ethyl acetate layer was washed with brine, dried (Na$_2$SO$_4$), filtered and concentrated in vacuo. The resulting product was purified by silica gel column chromatography using CH$_3$Cl$_3$:MeOH (50:1). The objective compound was obtained as a colorless oil (519 mg).

MS(m/z):423(m$^+$), 377, 331, 255, 138(BP), 91, 55.

(b) Synthesis of N-Carboxymethylslufonyl-(1S)-[2-(isoquinuclidin-2-yl)-2-oxo-ethyl]phenyl-ethylamine (compound 20)

A mixture of the compound (494 mg) obtained from the above mentioned Example 17 (a) and saturated $Na_2CO_3$ (3 mL) in EtOH (5 mL) was stirred for 12 h at room temperature. The reaction mixture was poured into saturated citric acid (50 mL) and extracted with $CHCl_3$ (50 mL×3). The $CHCl_3$ layer was washed with brine, dried ($Na_2SO_4$), filtered and concentrated in vacuo. The objective compound was obtained as a colorless crystal (121 mg).

IR($cm^{-1}$):3400, 3298, 1692, 1482, 1332, 1221, 1074, 618.
MS(m/z):335($m^+$−59), 313, 255, 138(BP), 91, 55.
$^1$H-NMR($CD_3OD$): 1.67–1.93 (9H, m), 2.36–2.61 (2H, m), 2.91 (2H, m), 3.36–3.42 (2H, m), 3.46–3.62 (2H, m), 3.64 and 4.37 (total 1H, each s), 3.65–3.84 (1H, m), 4.06–4.16 (1H, m), 7.23–7.32 (5H, m).

Example 18
Synthesis of N-[(2S)-2-benzyl-4-(isoquinuclidin-2-yl)-4-oxo-butanoyl]-2-aminothiazole (compound 3)

To a solution of the compound (80 mg) obtained from the above mentioned Example 1 in $CH_2Cl_2$ (3 mL) were added HOBt * $H_2O$ (49 mg), WSCDI (61 mg) and N-methylmorpholine (0.03 mL). The mixture was stirred at 0° C. for 1 h and N-methylmorpholine (0.04 mL) and 2-aminothiazole (40 mg) was added to the mixture. After stirring for 2 h, the reaction mixture was poured into saturated NaCl (50 mL) and extracted with ethyl acetate (50 mL×3). The ethyl acetate layer was washed with brine, dried ($Na_2SO_4$), filtered and concentrated in vacuo. The resulting product was purified by silica gel column chromatography using EtoAc. The objective compound was obtained as a colorless crystal (102 mg).

IR($cm^{-1}$):3424, 2926, 1683, 1608, 1548, 1452, 1170, 915, 867, 699.
MS(m/z):383($m^+$−1), 285(BP), 256, 231, 190, 153, 127, 95, 67.
$^1$H-NMR($CDCl_3$):0.87–1.91 (9H, m), 2.41–2.87 (3H, m), 3.11–3.27 (2H, m), 3.38 (2H, m), 3.67 and 4.48 (total 1H, each s), 6.91 (1H, d), 7.14–7.34 (5H, m), 7.46 (1H, d), 11.7 (1H, s).

Example 19
Synthesis of (4S)-4-benzyl-2-hydroxy-5-(isoquinuclidin-2-yl)-5-oxo-pentanoic acid (compound 41)

To a solution of the compound (730 mg) obtained from the above mentioned Reference 2 in $CH_2Cl_2$ (8.4 mL) was added aq $NaHSO_3$ (1.76 g) (6 mL) at 0° C. After stirring for 1 h, NaCN (691 mg) was added to the mixture and the mixture was stirred for 14 h at room temperature. The reaction mixture was poured into $H_2O$(50 mL) and extracted with ethyl acetate (5 mL×3). The ethyl acetate layer was washed with brine, dried ($Na_2SO_4$), filtered and concentrated in vacuo.

The residue was dissolved in EtOH (10 mL) and 10% KOH (5 mL) and the mixture was refluxed for 4 h. After concentrated in vacuo, the resulting residue was treated with 10% HCl to adjust the pH 2. The mixture was extracted with ethyl acetate (50 mL×3) and the ethyl acetate layer was washed with brine dried ($Na_2SO_4$), filtered and concentrated in vacuo. The resulting product was purified by silica gel column chromatography using $CH_3Cl_3$:MeOH (8:1). The objective compound was obtained as a colorless crystal (311 mg).

MS(m/z):311($m^+$), 286, 256, 242, 153, 117, 91 (BP).
$^1$H-NMR($CDCl_3$): 1.39–1.82 (11H, m), 2.23–3.70 (8.5H, m), 4.03–4.38 (1H, m), 4.42–4.50 (0.5H, m), 7.14–7.31 (6H, m)

Example 20
Synthesis of (4S)-4-benzyl-2-methoxymethyloxy-5-(isoquinuclidine-2-yl)-5-oxo-pentanoic acid (compound 43)

To a solution of the compound (150 mg) was obtained from the above mentioned Example 19 was dissolved in $CH_2Cl_2$ (8.4 mL) were added at 0° C. diisopropylamine (0.24 mL) and methoxymethyl chloride (0.1 mL). After stirring for 14 h, the reaction mixture was poured into $H_2O$ (50 mL) and extracted with ethyl acetate (50 mL×3). The ethyl acetate layer was washed with brine, dried ($Na_2SO_4$), filtered and concentrated in vacuo. The resulting product was dissolved in MeOH (10 mL) and 10% KOH (5 mL) was added and stirred at room temperature for 2 h. The reaction mixture was poured into 10% critic acid (50 mL) and extracted with ethyl acetate (50 mL×3). The ethyl acetate layer was washed with brine, dried ($Na_2SO_4$), filtered and concentrated in vacuo. The resulting product was purified by silica gel column chromatography using $CHCl_3$:MeOH (8:1). The objective compound was obtained as a yellow crystal (63 mg).

IR($cm^{-1}$):3540, 2938, 2860, 1725, 1596, 1452, 1215.
MS(m/z):375($m^+$), 330, 301, 256, 153, 117, 91(BP).
$^1$H-NMR($CDCl_3$):1.37–1.96(10H, m), 2.08–2.75 (3H, m), 2.80–3.66 (7.5H, m)

EFFECT OF THE INVENTION

The novel isoquinuclidine derivatives or the pharmaceutically acceptable salts in this invention has a potent blood glucose lowering activity and a safety, and it expect that useful as therapeutic and preventive agents of diabetes or diabetic complications.

What is claimed is:
1. A compound of formula (I) or a pharmaceutically acceptable salt,

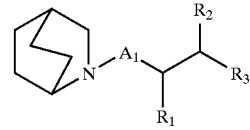

(I)

wherein, $A_1$ represents methylene or carbonyl, $R_1$ represents hydrogen or methyl group, $R_2$ represents —$(CH_2)_n$-$A_2$-Ph, wherein n denotes an integer of 0–3 and $A_2$ is single bond or —O—, $R_3$ represents —COOH, —$COOR_4$, —$COSR_4$, —$CONHR_5$, —$NHR_6$, —P(O) $(OPri)_2$, —$CH(R_9)$COOH, —$CH_2CH(COOH)_2$, —$SO_3H$, or a following formula:

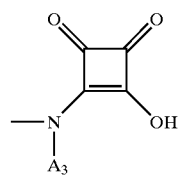

wherein, $R_4$ represents lower alkyl, non-substituted phenyl group, or phenyl group which is substituted with lower alkyl, lower alkoxy, hydroxy, methoxycarbonyl, ethoxycarbonyl, trifluoromethanesulfoneamide or halogen, $R_5$ represents pyridyl, thiazolyl, non-substituted phenyl group, or phenyl group which is substituted with lower alkyl, lower alkoxy, hydroxy, trifluoromethanesulfoneamide or halogen, $R_6$ represents —$SO_2$—$R_7$ or —CO—$(CH_2)_m$-$R_8$, wherein, $R_7$, represents lower alkyl, —$CH_2COOH$, trifluoromethyl, non-substituted phenyl, or phenyl group which is substituted with lower alkyl, lower alkoxy, hydroxy or halogen, $R_8$ represents carboxyl group, non-substituted phenyl, or phenyl group which is substituted with lower alkyl, lower alkoxy, carboxyl, hydroxy, halogen, —$NHSO_2CF_3$ or —NHCOCOOH, m=0 or 1, $R_9$ represents hydrogen, hydroxy or —$OR_{10}$ wherein $R_{10}$ is lower alkyl, —$CH_2OCH_3$, —$CH_2O(CH_2)_2OCH_3$ or —$CH_2SCH_3$, $A_3$ is hydrogen or methyl.

2. A method for preparing the compound of formula (III),

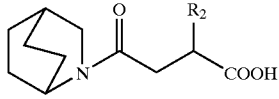

(III)

wherein, $R_2$ is —$(CH_2)_n$-$A_2$-Ph, wherein n denotes an integer of 0–3 and $A_2$ is single bond or —O—;

comprising condensation of a compound of formula (II),

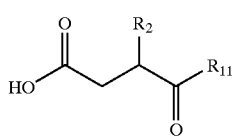

(II)

wherein, $R_2$ is the same as mentioned above; $R_{11}$ is 4(S)— or 4(R)-benzyl-2-oxazolidinone or 1(S)— or 1(R)-2,10-camphorsultam, with isoquinuclidine followed by removal of a chiral auxiliary ($R_{11}$).

3. A method for preparing the compound of formula (V),

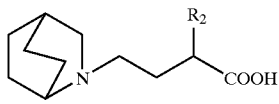

(V)

wherein, $R_2$ is —$(CH_2)_n$-$A_2$-Ph, wherein n denotes an integer of 0–3 and $A_2$ is single bond or —O—;

comprising reduction of a compound of formula (II)

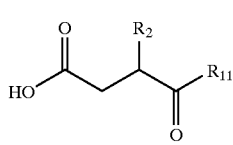

(II)

wherein, $R_2$ is the same as mentioned above; $R_{11}$ is 4(S)— or 4(R)-benzyl-2-oxazolidinone or 1(S)— or 1(R)-2,10-camphorsultam; with a reductant to yield a compound of formula (IV),

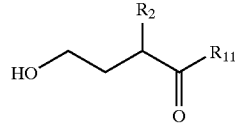

(IV)

wherein, $R_2$ and $R_{11}$ are the same as mentioned above; then the hydroxy group is methylated or halogenated followed by reaction with isoquinuclidine and removal of the chiral auxiliary ($R_{11}$).

4. A method for preparing the compound of formula (VII),

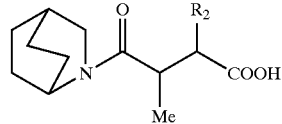

(VII)

wherein, $R_2$ is —$(CH_2)_n$-$A_2$-Ph, wherein n denotes an integer of 0–3 and $A_2$ is single bond or —O—;

comprising condensation of a compound of formula (VI),

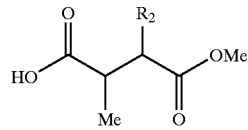

(VI)

wherein, $R_2$ is the same as mentioned above; with isoquinuclidine followed by hydrolysis of the ester.

5. A method for preparing the compound of formula (IX),

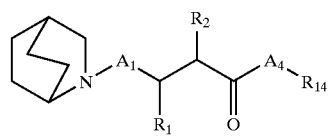

(IX)

wherein, $A_1$ represents methylene or carbonyl, $R_1$ represents hydrogen or methyl group, $R_2$ represents —$(CH_2)_n$-$A_2$-Ph, wherein n denotes an integer of 0–3 and $A_2$ is single bond or —O—, $R_4$ represents lower alkyl, non-substituted phenyl group, or phenyl group which is substituted with lower alkyl, lower alkoxy, hydroxy, methoxycarbonyl, ethoxycarbonyl, trifluoromethanesulfoneamide or halogen, $R_5$ represents pyridyl, thiazolyl, non-substituted phenyl group, or phenyl group which is substituted with lower alkyl, lower alkoxy, hydroxy, trifluoromethanesulfoneamide or halogen;

$R_{14}$ is $R_4$ or $R_5$, and $A_4$ is —O—, —S—, or —NH—; comprising condensation of a compound of formula (VIII), (VIII)

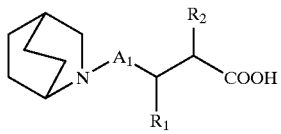

wherein, $A_1$, $R_1$, and $R_2$ are the same as mentioned above; with $R_4OH$, $R_4SH$ and $R_5NH_2$.

6. A method for preparing the compound of formula (XII), (XII)

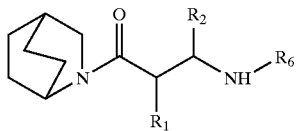

wherein, $R_1$ represents hydrogen or methyl group, $R_2$ represents —$(CH_2)_n$-$A_2$-Ph, wherein n denotes an integer of 0–3 and $A_2$ is single bond or —O—, $R_6$ represents —$SO_2$—$R_7$ or —CO—$(CH_2)_m$—$R_8$ wherein, $R_7$ represents lower alkyl, —$CH_2COOH$, trifluoromethyl, non-substituted phenyl, or phenyl group which is substituted with lower alkyl, lower alkoxy, hydroxy or halogen, $R_8$ represents carboxyl group, non-substituted phenyl, or phenyl group which is substituted with lower alkyl, lower alkoxy, carboxyl, hydroxy, halogen, —$NHSO_2CF_3$ or —NHCOCOOH, m=0 or 1;

comprising condensation of a compound of following formula (X), (X)

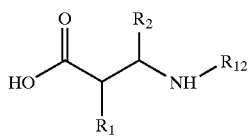

wherein, $R_1$ and $R_2$ are the same as mentioned above; $R_{12}$ is benzyloxycarbonyl group or tert-butoxycarbonyl group; with isoquinuclidine followed by deprotection of the amino group to give a compound of following formula (XI), (XI)

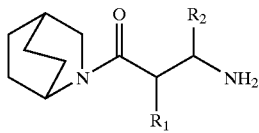

wherein, $R_1$ and $R_2$ are the same as mentioned above; and the compound of general formula (XI) is reacted with $R_7SO_2Cl$, or $R_{13}$—CO—$(CH_2)_m$-$R_8$ wherein $R_7$ and $R_8$ are the same as mentioned above; $R_{13}$ is halogen, OH, or OMe, or $HP(O)(OPri)_2$.

7. A method for preparing the compound of formula (XIII), (XIII)

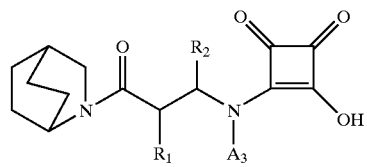

wherein, $R_1$ represents hydrogen or methyl group, $R_2$ represents —$(CH_2)_n$-$A_2$-Ph, wherein n denotes an integer of 0–3 and $A_2$ is single bond or —O—, $A_3$ is hydrogen or methyl;

comprising reaction of a compound of formula (XI)

(XI)

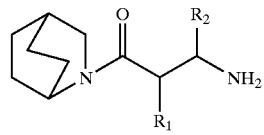

wherein, $R_1$ and $R_2$ are the same as mentioned above; with diisopropylsquarate optionally followed by N-methylation, and hydrolysis with acid.

8. A method for preparing the compound of formula (XVI), (XVI)

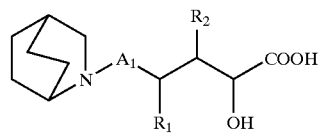

wherein, $A_1$ represents methylene or carbonyl, $R_1$ represents hydrogen or methyl group, $R_2$ represents —$(CH_2)_n$-$A_2$-Ph, wherein n denotes an integer of 0–3 and $A_2$ is single bond or —O—, comprising reduction of a compound of formula (XIV), (XIV)

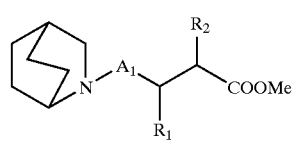

wherein, $A_1$, $R_1$, and $R_2$ are the same as mentioned above; followed by oxidation to give a compound of following formula (XV), (XV)

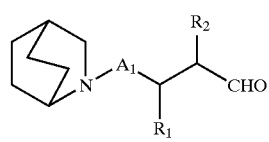

wherein, $A^1$, $R_1$, and $R_2$ are the same as mentioned above; and the compound of general formula (XV) is reacted with NaCN or KCN followed by hydrolysis of nitrile group.

9. A method for preparing the compound of formula (XVII),

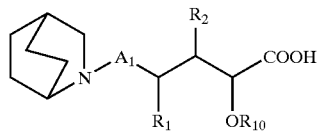
(XVII)

wherein,
$A_1$ represents methylene or carbonyl,
$R_1$ represents hydrogen or methyl group,
$R_2$ represents —$(CH_2)_n$-$A_2$-Ph, wherein n denotes an integer of 0–3 and $A_2$ is single bond or —O—,
$R_{10}$ is lower alkyl, —$CH_2OCH_3$, —$CH_2O(CH_2)_2OCH_3$ or —$CH_2SCH_3$; comprising reaction of a compound of formula (XVI)

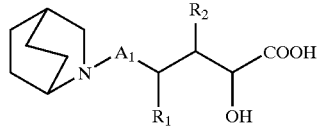
(XVI)

wherein, $A_1$, $R_1$, and $R_2$ are the same as mentioned above; with $R_{10}$—X (X is halogen) followed by hydrolysis of its ester group.

10. A method for preparing the compound of formula (XVIII),

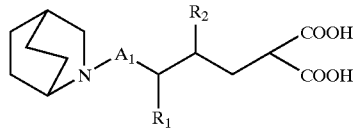
(XVIII)

wherein,
$A_1$ represents methylene or carbonyl,
$R_1$ represents hydrogen or methyl group,
$R_2$ represents —$(CH_2)_n$-$A_2$-Ph, wherein n denotes an integer of 0–3 and $A_2$ is single bond or —O—;
comprising reaction of a compound of formula (XV)

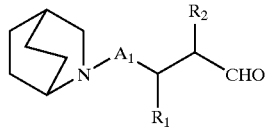
(XV)

wherein, $A_1$, $R_1$, and $R_2$ are the same as mentioned above, with $CH_2(COOMe)_2$, followed by hydrogenation and hydrolysis.

11. A method for preparing the compound of formula (XIX),

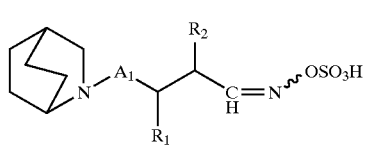
(XIX)

wherein,
$A_1$ represents methylene or carbonyl,
$R_1$ represents hydrogen or methyl group,
$R_2$ represents —$(CH_2)_n$-$A_2$-2h, wherein n denotes an integer of 0–3 and $A_2$ is single bond or —O—;
comprising reaction of a compound of formula (XV)

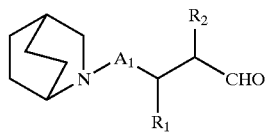
(XV)

wherein, $A_1$, $R_1$, and $R_2$ are the same as mentioned above, with $H_2NOSO_3H$.

12. A pharmaceutical composition comprising compounds of formula (I) or their pharmaceutically acceptable salts, according to claim 1, as active ingredients which have blood glucose lowering activity.

* * * * *